(12) United States Patent  
Hammesfahr

(10) Patent No.: US 6,258,032 B1
(45) Date of Patent: Jul. 10, 2001

(54) METHOD OF DIAGNOSIS AND TREATMENT AND RELATED COMPOSITIONS AND APPARATUS

(75) Inventor: William M. Hammesfahr, 600 Druid Rd. East, Clearwater, FL (US) 34616

(73) Assignee: William M. Hammesfahr, Clearwater, FL (US)

( * ) Notice: Subject to any disclaimer, the term of this patent is extended or adjusted under 35 U.S.C. 154(b) by 0 days.

(21) Appl. No.: 09/101,934
(22) PCT Filed: Jan. 29, 1997
(86) PCT No.: PCT/US97/01576
 § 371 Date: Jul. 13, 1998
 § 102(e) Date: Jul. 13, 1998
(87) PCT Pub. No.: WO97/27745
 PCT Pub. Date: Aug. 7, 1997
(51) Int. Cl.[7] ........................................................ A61B 8/06
(52) U.S. Cl. ............................................. 600/454; 600/504
(58) Field of Search .................................... 600/453–456, 600/437, 504–507; 604/21, 30, 31, 49–50

(56) References Cited

U.S. PATENT DOCUMENTS

| | | | |
|---|---|---|---|
| 4,163,790 | * | 8/1979 | Franko et al. ......................... 424/267 |
| 5,278,192 | * | 1/1994 | Fung et al. ............................ 514/645 |
| 5,634,895 | * | 6/1997 | Igo et al. .............................. 604/21 |
| 5,731,339 | * | 3/1998 | Lowrey ................................ 514/400 |

* cited by examiner

Primary Examiner—Francis J. Jaworski
(74) Attorney, Agent, or Firm—Richard Coale Willson, Jr.

(57) ABSTRACT

A method for treatment of a disease comprising vasospasm or other symptom alleviable by smooth muscle relaxation and a vasodilator delivery system. The figure is a TCD of MCA post nitroglycerine spray obtained during continuous monitoring.

14 Claims, 5 Drawing Sheets

TCD of MCA immediately prior to nitroglycerine spray administration.

Figure 1 TCD of MCA immediately prior to nitroglycerine spray administration.

Figure 2 TCD of MCA post nitroglycerine spray obtained during continuous monitoring Figure 3   Raw EEG Data

METHOD OF DIAGNOSIS AND TREATMENT AND RELATED COMPOSITIONS AND APPARATUS

RELATED APPLICATIONS

This application claims priority of the provisional application filed Jan. 31, 1996 as No. 60/010,881 of the United States Patent and Trademark Office.

BACKGROUND OF THE INVENTION

I. Field of the Invention

This invention deals with medicine and the diagnosis and treatment of certain types of blood vessel diseases and a variety of disorders which all have been discovered to have in common a condition called "Vasospasm" or "Narrowing of the Blood Vessels."

II. Description of the Prior Art

The most relevant prior art appears to be:
1. Roger P. Woods, Marco Iacoboni, M.D., Ph.D., and John C. Mazziotta, M.D., Ph.D.; Brief Report: Bilateral Spreading Cerebral Hypoperfusion during Spontaneous Migraine Headache. N Engl J Med 1994; 331; 1689–92.
2. M. Hennerici, M.D., W. Rautenberg, M.D., G. Sitzer, M.D., and A. Schwartz, M.D.; Transcranial Doppler Ultrasound for the Assessment of Intracranial Arterial Flow Velocity—Part 1, Examination Technique and Normal Values; Surg Neurol 1987; 27; 439–48.
3. U.S. Pat. No. 5,309,923 to Leuchter and Cook, U.S. Pat. No. 5,307,807 to Sosa et al, U.S. Pat. No. 5,287,859 to Erwin describe "qEEG" devices and techniques useful with the invention.
4. U.S. Pat. No. 5,163,444 to Braverman discusses the P300 brain waves mentioned below.

III. Problems Presented by Prior Art

Prior treatment regimens have generally focused on the acute disease while the present invention embodies the discovery that the vasospasms and vascular narrowings are commonly chronic in nature. Further, past dosages have often been excessive and such over-dosages are found by applicant's investigations to actually be harmful in patients at some stages, because such dosages can themselves subtlety promote vasospasms.

SUMMARY OF THE INVENTION

I. General Statement of the Invention

It is an object of this invention to treat vascular spasm as identified primarily from ultrasound, but which may be suspected on the clinical grounds, with the use of vasodilators in a progressive step-wise fashion, preferably titrated against continuing testing. The introduction usage of the medications and tapering of the medications must be done in a specific fashion in order to result in a clinical improvement of the patient in a variety of conditions which all have in common the presence of vascular spasm. Certain of these conditions have not previously been identified as having vascular spasm as a component of their disorder, and these conditions have been identified in applicant's clinical practice and thus will be named further under the section that deals with claims. It has been recognized that patients with vascular spasm have a typical clinical presentation of symptoms, and that these symptoms follow a progression in substantially direct correlation to the vascular spasm identified on Transcranial Doppler (TCD), a technique using ultrasound imaging of the brain for evaluation of vascular size. It is further recognized clinically that vascular dilation medications may have paradoxical responses depending upon dose. In essence, there is a therapeutic window, a dose which is the proper dose for treatment of the condition which changes over time. Initially under dosing the patient will result in no change of their symptoms, as well as overdosing the patient will result in the exact same symptoms as under dosing the patient or giving the patient no medication at all. Thus vascular dilation medications tend to have a paradoxical response with overdose. The proper dosage for a patient is based upon clinical response in association with objective data as may be identified from Transcranial Doppler ultrasound as well as other imaging modalities.

Essentially the preferred methodology is to obtain an image or measurement of the intracranial blood vessels in the diseased conditions to be noted under claims, and then introduce low dose vasodilation medications. Repeat ultrasounds or other imaging modalities are used to titrate the patient's medical response. As vascular dilatation occurs, medications hen become altered in a stepwise tapering fashion, using ultrasound or other imaging modalities to identify the redevelopment of vasospasm and the appropriate dosage of medication. It is recognized that patients' metabolism may vary across the course of the time that they are on these medications, and it is further recognized that patients' clinical symptoms may not be a useful guide to their response to medication. Accordingly, repeat evaluations with the use of imaging modalities are used to assess pharmacological response.

The invention comprises a method of treating a patient presenting with symptoms suggestive of a stroke or multiple sclerosis (MS) and/or reporting trauma to the neck and/or head e.g. whiplash or concussion from a fall or any other disease discovered to be alleviatable by relaxation of smooth muscle or to comprise vasospasm, preferably intracranial vasospasm as a symptom; comprising in combination:
a) testing by determining rate of blood flow, preferably intercranially or in the arteries of the neck and or upper back, and/or determining relative diameter of those vessels e.g. by magnetic resonance imaging (NMRI) and/or determining evoked potential;
b) treating the patient with an effective dosage of a vasodilator, preferably nitroglycerin administered by patch, preferably at a rate less than about 0.8 mg/hr;
c) re-determining said rate or diameter or potential (collectively "blood flow") after said treatment, to evaluate recurrence of vasospasm;
d) adjusting the dosage in response to the results of the re-determining;
whereby symptoms comprising headache, burning sensation or pain in the head dizziness, or fainting, etc., or other symptoms of the disease treated, are alleviated.

Disease:

The technique and associated compositions are valuable in the treatment of any condition in which vasospasms, preferably cerebral vasospasms are detected as a component, including without limitation, those conditions listed under Utility of the Invention.

Symptoms:

The common symptom to all these conditions is the vasospasm, particularly cerebral vasospasm.

Testing:

Transcranial Doppler is the most preferred test, both for diagnosis and also for titrating dosage of the vasodilators preferred for treatment. Other tests will preferably be used as discussed under Methodology. Generally intracranial blood velocities greater than 0.6 meters/ second, are indicative of vasospasm. Generalized cerebral vasospasm is identified by TCD Mean Flow Velocities (MFV) of greater than 0. 1, more preferably than 0.3 and particularly greater than 0.4 meters/second in intracranial vessels (about 0.07, 0.2 and 0.4 meters/second, respectively, for vertebrobasilar system) and prolonged diastolic flow component in which continued elevation of diastolic flow beyond end diastolic velocity occurs throughout substantially the entire course of diastole. This prolonged diastole is the most preferred indicator of vasospasm. Other presently available tests which are valuable for vasospasm detection and dosage titration comprise SPECT nuclear medicine testing, angiograms, EEG, qEEG, P300, and other neuropsycological, psychological and electrophysiological tests which can monitor mental impairment due to vasospasm.

Vasodilator:

Nitroglycerine is the most preferred vasodilator for the treatment of the invention, both because of its ready availability in a variety of forms; pill, patch, ointment, cream, spray, inhaler, etc., and because its pharmacology is so well known. The many Nitroglycerine equivalents and substitutes, such as p.o. clonidine, Dynacirc (isradipine), hydrazine, or long acting nifedipine and others known to the art, can be used to replace or to supplement Nitroglycerine. For patients exhibiting Nitroglycerine intolerance, a combination of Nitroglycerine (spray or patch) with Nifedipine is particularly preferred.

Alpha blockers have been tried. Hytrin (Terazosin) has not been found to be effective. Catapress (Clonidine) has been extremely effective. Minipress (Prazosin) has been significantly effective and frequently better tolerated in the long run than Clonidine, although in Applicant's patients, it seems to treat the problem successfully enough to prevent the symptoms, but not enough to allow complete resolution of the vasospasm. Cardura (Doxazosin) has been a relatively mild medication. Aldomet (Methyldopa) has been useful in some patients. Reserpine has been an extremely effective medication. In the short term, it is helpful due to the parasympathomimetic effect, which tends to decrease the activity of the Sumpathetic nervous system. Later, its direct sympatholytic action is very effective. Frequently, a dose needs to be adjusted downward approximately 6–10 weeks after institution of therapy. It has even been useful in treating migraine induced depression due to chronic vasospasm with or without headache in those patients who could not tolerate other vasodilators. Clonidine has also been useful in these depressed patients who could not respond to other vasodilating medications.

ACE inhibitors are effective. With use of ACE inhibitors and concomitant administration of low dose Nitroglycerin, 1/10th inch once a day to several times a day, most patients may be eventually weaned from the use of oral medications, although Applicant does tend to maintain them on low dose Nitroglycerin in perpetuity. Other Angiotensin Converting Enzyme Inhibitors, including Capoten (Captopril), Altace (Ramipril), Lotensin (Benazepril), Monopril (Fosinopril), Prinivil (Lisinopril), Vasotech (Enalapril), and an ACE inhibitor have also been tried. Applicant suspects that ACE inhibitors work the best due to their activity on the Nitric Oxide pathway. They are most effective at reversing the vasospasm when used in conjunction with low dose nitrates.

Calcium channel blockers are effective. The most effective has been Dynacirc (Isradapine). Much less effective have been, in descending order of effectiveness, Nifedipine, Nimodopine, Plendil (Felodipine), Dilacor (Diltiazem), Cardene (Nicardipine) and, Norvasc (Amlodopine) and finally, Verapamil.

Other agents that deserve special mention include Toradol IM in doses of 90–120mg. In lower doses, this is not so effective. Unfortunately, due to the new FDA guidelines, Applicant no longer uses this medication in these doses. Hydralazine is effective, but tends to cause significant blood pressure changes in these patients. Interestingly though, Hydralazine tends to improve the morphology of the diastolic flow component dramatically, which in view of Hydralazine's effect on arterioles, bolsters the perspective that the diastolic phase of the Transcranial Doppler is a good indicator of downstream runoff.

Psychiatric agents frequently have vasoactive effects. Prozac, and other non-vasoconstricting medications are helpful.

As examples of the many drugs available: Clonidine has been extremely effective. Hytrin (Terazosin), Ismelin (Guanethidine), Minipress (Prazosin), have been all tried, with less successful results. Cardura (Doxazosin) is still being tried, but initial results are just now coming available. Dibenzyline (Phenoxybenzamine) beta blockers, Inderal (Propranolol), Tenormin (Atenolol), Normodyne (Labetolol), Lopressor (Metoprolol) Imitrex (Sumatriptan), IM Toradol (Ketorolac) Channel Blocker, and an ACE inhibitor along with low dose Nitroglycerine and a Clonidine patch, as well as magnesium, Brethine, etc.

Accupril (Quinapril), Altace (Ramipril), Capoten (Captopril), Lotensin (Benazepril), Monopril (Fosinopril), Prinivil (Lisinopril), Zestril (Lisinopril timed released), Univasc (Moexipril), Vasotec (Elalapril), Cozaar (Losartan). Accupril (Quinapril) has Inderal (Propranolol), Tenormin (Atenolol), Normodyne (Labetolol), Lopressor (Metoprolol) Angiotensin Converting Enzyme Inhibitors (ACE) inhibitors have been tried including Accupril (Quinapril), Altace (Ramipril), Capoten(Captopril), Lotensin (Benazepril), Monopril (Fosinopril), Prinivil (Lisinopril), Zestril (Lisinopril timed released), Univasc (Moexipril), Vasotec (Elalapril), Cozaar (Losartan). Accupril (Quinapril) has consistently been the most effective. p.o. clonidine, Dynacirc (isradipine), hydrazine, Adalat (Nifedipine) in standard doses and timed release dosages has been helpful but as a second line drug. Careen (Nicardipine), Nimotop (Nimodopine), Cardizem (Diltiazem), Norvasc (AmlodipineMellaril (Thioridizine) has not been effective. Thorazine Chlorpromazine) has been moderately effective. Navane (Thiothixene) has been extremely effective.

All of the effective medications have the common characteristic of causing smooth muscle relaxation and reduce pulmonary capillary wedge pressure in most cases, which empirically defines a class of useful medications which also includes many other medications, some of which are setforth in Appendix A, filed with this application.

Dosage:

It is an important feature of the invention that the vasodilator dosage is substantially lower than dosage usually prescribed for treatment of coronary disease, preferably about 1 to 40%, more preferably 5 to 30, and most preferably 10 to 25% of such conventional dosage. Based on a 70 kilogram patient, on a Nitroglycerine-equivalent basis, about 0.001 to 5000, more preferably about 0.01 to 1000 and most preferably 0.02 to 20 milligrams per day of vasodilator will be optimal in most cases. Still lower rates will be employed on pediatric, and lower body weight adult, patients. Stated differently, from about 10 minutes to 20 hours or even more per day of application of a commercial Nitroglycerine patch can be administered during initial treatment. Further, this dosage will be optimized by reducing or increasing the dosage in response to continuing test results, particularly TCD and qEEG, showing reduction in frequency and/or severity of the patient's vasospasms. In most cases, just sufficient vasodilator will be administered to achieve optimum reduction in vasospasms (preferably measured as optimal TCD Mean Flow Velocity (MFV) at the respective stage of treatment. It will be recognized that these dosages are mainly far lower than the vasodilator dosages commonly employed to treat cardiac disease and this is because the treatment of vasospasm needs much lower dosage, and that vasospasm may even be induced by the vascular reaction to high dosages of vasodilator. Without being bound to any theory, it appears that the number of receptors increases during treatment, so that some patients are able to tolerate only lower dosages as treatment continues. Thus, the "titration" of dosage from time to time on the basis of test results is stressed in the present application.

Duration:

Because of the discovery that the vasospasms are not merely acute, but are chronic, treatment duration will be prolonged in most cases, extending over months and even years in some cases. Typically treatments will extend over about 5 to 250 weeks, more preferably 8 to 100, and most preferably 12 to 60 weeks, though treatment duration will be controlled by the patient's response as indicated by the continuing testing.

Titration:

Frequent testing, as much as even several TCDs in a single day during initial treatment, will be used to titrate dosage so as to avoid overdose (which can itself trigger vasospasms) as the patient's condition improves.

Delivery Systems:

The average dosage on a typical patient will be in the range of roughly one milligram per day. It is desirable to have delivery systems, sprays, ointments, creams, inhalers, and preferably patches of reduced delivery as compared to the conventional systems now available commercially. Such reduced delivery systems are particularly desirable for patients who tend to be too noncompliant, e.g. mentally impaired, to follow reliably a treatment regimen of intermittently applying and removing conventional patches to reduce dosage. Such vasodilator delivery systems will preferably be marked (or packed) with the appropriate DRG and/or ICD 9th. codes and/or instructions for titrating and tapering their use, to facilitate their proper application.

1. Utility of the Invention

This technique is useful in treating a variety of conditions including closed head injury with vasospasm, attention deficit disorder with vasospasm, migraine with inter-ictal evidence of vasospasm, syncope or blackout spells of unknown aetiology with evidence of vasospasm, seizure with evidence of vasospasm, and dementia with evidence of vasospasm, and post-concussion syndrome with evidence of vasospasm, migraine, post-concussion syndrome, sympathetic vasospasm associated with breast implants, and cerebral vasospasm. The invention embodies the discovery that such vasospasms are a component symptom of many whiplash injuries.

While less studied at present, the invention can be used to diagnose and treat the following other diseases which have now been found to frequently involve vasospasms: neurocognative disorders such as, dyslexia, memory disturbances, depression, psychosis, reflex sympathetic dystrophy, mood disorders and sensory motor disorders; transient ischemic attack (TIA), pseudoseizure, hemibalism, and stroke; tremor, Parkinson's disease, torticollis, electrical shock trauma, as well as any other disease in which vasospasm can be detected as a component of symptoms. Even cases of Benign Prostate Hypertrophy (BPH) can be treated with the vasodilators of the invention to relax the smooth muscle of the sphincter (where the vasodilator relaxes the muscle even where vasospasm is not a symptom) allowing better emptying of the bladder. Further clinical testing has also established the usefulness in some cases, of additional diseases which have now been found unexpectedly to involve a substantial degree of vasospasm, comprising; vertigo, autism, depression, psychosis, transient global amnesia, memory disabilities, balance disabilities, Tourette's Syndrome, Tinnnitis, Multiple Sclerosis and Multiple Sclerosis-like syndrome, hyperactivity and Attention Deficit Disorder, deficits resulting from strokes of various causes, migraine, seizures, balance disorders, concussion, post-concussion syndrome sometimes including temporal mandible joint pain (TMJ) or facial pain, cerebral ischemia and other vascular components discovered to be associated symptoms in some cases of psychiatric disorders such as chronic depression and some psychosis, as well as vascular dysfunction from any cause such as kidney disease and peripheral vascular disease e.g. from diabetes, cholesterol, infection or other cause. A basic factor is that neurological diseases are really symptom diagnoses for the most part. Thus depression is the diagnosis for a specific type of behavioral abnormality, not the underlying pathological or anatomical diagnosis. This is also true for stroke, multiple sclerosis, vertigo, balance disorders, and many other diseases may be directly caused by ischemia, or have a component of their problem caused by ischemia, or have associated problems caused by vasospasm arising from their associated problems.

DESCRIPTION OF THE PREFERRED EMBODIMENTS

EXAMPLES

Whiplash, MS, Migraine

Figure 1:
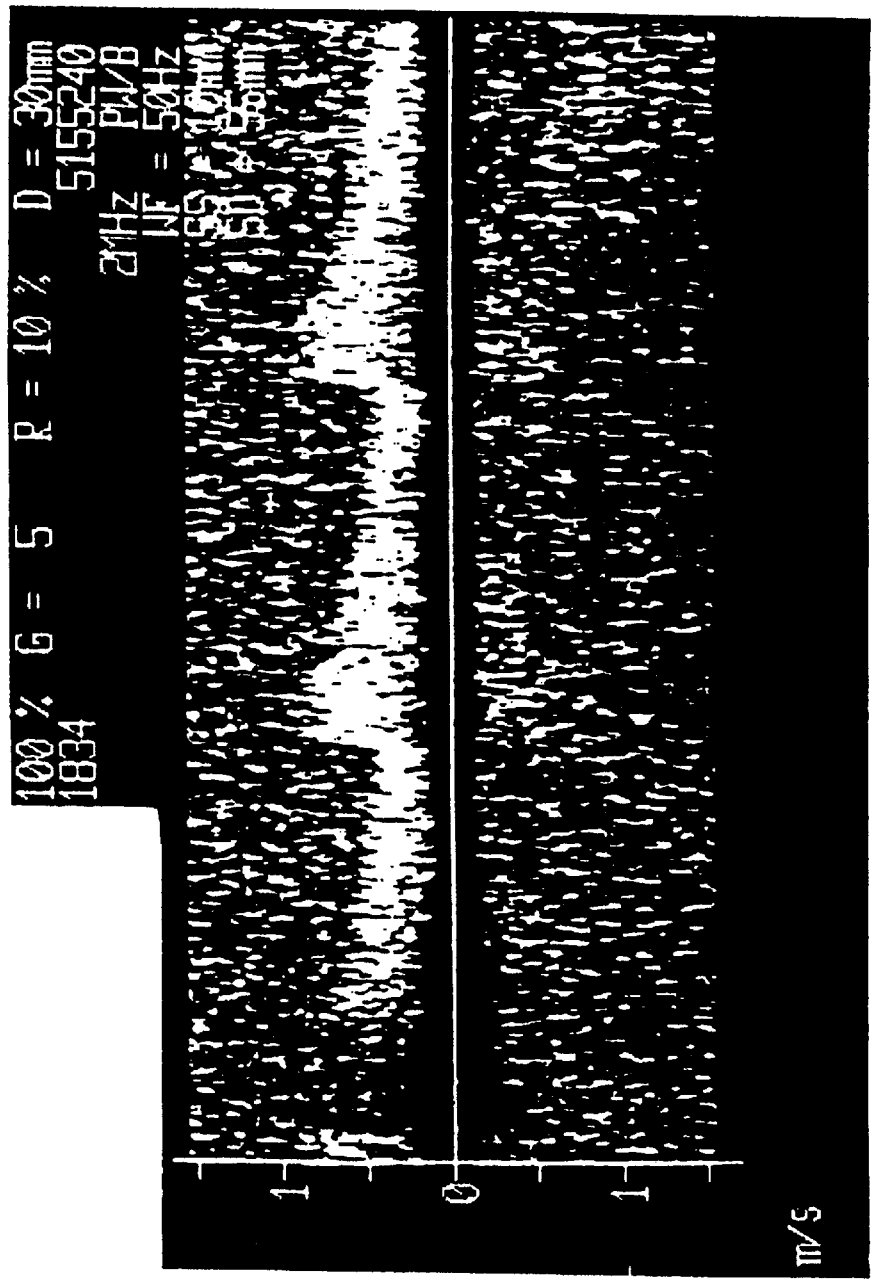
FIG. 1 is a Transcranial Doppler (TCD) of MCA immediately prior to treatment by Nitroglycerine spray.

A clinical review and correlation among 38 whiplash patients, 19 patients with MS-like syndrome, one with MS associated with breast implants, as well as 5 migraine patients is presented. All patients have similar clinical complaints, EEG abnormalities, and cerebral vasospasm identified on Transcranial Doppler testing. All have similar clinical responses to medication that resulted in clinical improvement paralleling the course of clinical resolution of the cerebral vasospasm.

Methodology:

All patients are evaluated with a complete history, physical exam, and neurological exam by a Board Certified Neurologist. All patients have blood work consisting of a CBC with differential count and platelets as well as an SMA-30 obtained. All whiplash related patients underwent a CT or MRI of the brain, EEG and qEEG, B-mode and spectral analysis ultrasound of the subclavian, carotid, and vertebral circulation, and Transcranial Doppler (TCD) examination of the intracranial circulation. In some situations, repetitive Transcranial Doppler examinations are performed on the same patient in the same day. Initially, these tests are performed by maintaining the probe on the patient's head through the course of several hours, but later the technique involves using the same probe, patient position, technician, depth, and cranial window with serial but interrupted exams across the course of the day. In all cases, the highest spectral frequencies are recorded, as well as repeat exams at the same depth and window as the baseline pre-medication windows were obtained. Immediately prior to initial TCD exams, a neurological exam is carried out. At the time of initiation of treatment for the cerebral vasospasm, at which time vasoactive medications are administered after the baseline TCD and neuro exam are obtained, repeat TCD exams are carried out and when medication effects on the intracranial circulation were identified, repeat neurological exams are obtained. In 5 patients, P300 are obtained prior to initiation of treatment and, again, several months later. The same methodology is used in those patients referred for evaluation of possible MS-like syndrome as recognized in the recent global settlement. With these patients, triple evoked potentials, EEG and qEEG, and a vascular evaluation as outlined above is carried out in all patients, and in 11 who decided to attempt treatment with vasoactive drugs, the methodology outlined above for initiation of as in the MVA-related post-concussion syndrome are used. 10 of the 19 MS-like syndrome patients additionally had brain MRI tests performed. In 3 of the MS-like syndrome patients, P300 tests are obtained and serial studies after 1–2 months of treatment in all 3 were also obtained. The same methodology are also used with respect to the patients with a history of migraine, although only two of these had MRI or head CT exams performed at time of initiation of treatment. All 5 had carried a diagnosis of migraine headache for at least 10 years prior to evaluation.

All patients noted that these symptoms are intermittent in occurrence, and at times some symptoms would coexist with other symptoms, and at other times these symptoms would be dissociated each from the other. All noted that the symptoms could be aggravated by stress. All patients had tried over the counter and prescription anti-inflammatories and muscle relaxants prior to and during the initial stages of evaluation without significant relief. All had been tried on Fioricet or Fiorinal, Midrin (isometheptene mucate), and aspirin. 22 of the 38 patients had also been tried on calcium channel blockers, beta blockers, Imitrex (sumatriptan succinate), and p.o. Toradol (ketorolac tromethamine). 21 of the 38 used narcotics for pain control. Neurological exam on these patients are remarkable, during exacerbation, for lower extremity hyperreflexia, abnormal tandem gait, and abnormal Rhomberg exam. All patients' examinations could be aggravated by inducing psychological stress in the patients or performing actions that increased their pain, as would occur by doing activities that would aggravate their neck discomfort. All patients had normal MRI or CT examination of the brain. EEG and qEEG exams are performed on each of these patients, with the following findings. All patients had a low voltage 5–20 microvolt polymorphic delta and theta pattern identified in the frontal and temporal areas. Those who complained of ataxia and balance disturbance had the same abnormalities identified in the occipital lobe. All had a superimposed mu rhythm in the frontal and temporal areas better identified on qEEG than on bipolar montages as this rhythm appeared as a subharmonic superimposed over the posterior occipital alpha rhythm on the bipolar montage. The qEEG, a 16 channel average referential montage, allowed improved definition of wave form analysis and spatial distributions and confirmed the underlying EEG evaluations. TCD exams in all patients showed evidence of generalized cerebral vasospasm as identified by Mean Flow Velocities (MFV) of greater than 0. 1, more preferably 0.2 and most preferably 0.4 meters/second in intracranial vessels (about 0.06, preferably 0.2 and most preferably 0.3 meters/second for vertebrobasilar system) and prolonged diastolic flow component in which continued elevation of diastolic flow beyond end diastolic velocity occurs throughout the entire course of diastole. In all cases, the EEG and qEEG abnormalities mirrored the distribution of vascular abnormalities identified on Transcranial Doppler.

Results:

38 patients referred with post-concussion syndrome after whiplash due to fall, motor vehicle accident (MVA), or beating are evaluated. On initial evaluation, their clinical complaints included intermittent headache, photophobia, visual blurring or transient scotomas, hyperacusis, word finding or word substitution problems, ataxia or balance disturbance, memory and concentration lapses, and, in some cases, black out spells associated with syncope. A baseline blood pressure, neurological exam and TCD are then obtained at the time of initiation of treatment, and treatment are initiated with nitroglycerin sublingual spray. Initially, continuous TCD monitoring was performed for out to two hours from administering the spray. Continuous monitoring was performed of that vessel previously identified to be in the most severe spasm. Ongoing monitoring of blood pressure and pulse with an electronic monitor was also performed. When pharmacological relaxation had peaked, repeat neurological exams are performed as well as patient's clinical perspectives on their symptoms are sought.

All patients showed improvement in Mean Flow Velocities at 15 minutes who are continuously monitored, and the peak degree of relaxation was seen at 1 hour with continued relaxation of the intracranial spasm identified out to two hours. At the time of peak relaxation, approximately 1–2 hours out from administration of the nitroglycerin or other vasoactive drugs, a full TCD and neurological exam was carried out. No blood pressure changes, including orthostatic changes, of significance are noted as defined as changes in systolic or diastolic readings of 10 points or greater and changes in pulse of 10 points or greater. Generally no changes in pulse or blood pressure are noted beyond changes of less than 5 points in any of the readings. Continuous TCD monitoring was performed in 9 patients. Serial TCD monitoring was performed in 25 patients, usually at 45–60 minutes post administration. All patients showed clinical improvement, however 3 patients did not show significant TCD improvement. These patients are subsequently identified as unable to tolerate Nitroglycerine and are nitrite sensitive. In those patients who are continuing to be monitored, they redeveloped their subjective symptoms and objective exam abnormalities as the vasospasm returned as documented on TCD.

The TCD exam became vital for individualizing treatment. It was found that the therapeutic window for Nitroglycerine changed over the first 3 months of treatment and patients frequently redeveloped their symptoms or developed migraine headaches. Here the TCD was vital for modifying treatment. In these patients, while on Nitroglycerine, a repeat TCD is obtained and then a therapeutic challenge is administered by spray. Repeat TCD is obtained at 15 minute and 1 hour intervals. Those patients who had developed a Nitroglycerine-induced migraine or migraine equivalent mirroring or superimposed on their original problem developed worsening of the TCD at the 15 minute or the 1 hour interval. Those who required increases in their dose, showed improvement of Mean Flow Velocity on TCD. 1 patient who had previously failed Nitroglycerine spray or patch alone due to a nitrite sensitivity, and failed Nifedipine alone, is able to tolerate the two in a combined dose with virtual complete resolution of clinical symptoms as confirmed by history, exam, and TCD findings. With removal of the Nitroglycerine, while any degree of abnormalities are still seen on TCD, applicant's patients' problems recur. However, with continuing treatment until Mean Flow Velocity has returned to normal and is documented as normal during Nitroglycerine free intervals during the day, the patients could then use the Nitroglycerine spray or patch on a PRN basis for treatment of any of the above mentioned complaints with great success rather than continuing to require scheduled daily doses of medication.

While most patients eventually reached a peak daily dosage of 4–6 hours in two to three divided doses on a nitroglycerin patch during treatment, dosage requirements varied from 10 minutes a day in two adolescent girls, and one 30 year old male, up to a total of 24 hours a day for one 34 year old woman whose initial complaints prior to starting the Nitrodur (nitroglycerin) patch included severe ataxia, confusion and intermittent syncope or episodes of hemiparesis in addition to the visual blurring, headaches and concentration and memory changes seen in the other patients.

Most patients are on this dose for 1–2 months, and then tapered. No patients who are able to tolerate Nitroglycerine treatment continued to require narcotics, and only two of the above patients in this series remained on narcotics where 21 of the 38 who started treatment are on narcotics for pain control. Of great significance is that 2 patients with intermittent syncope also have episodic hemiplegic migraines. They showed complete resolution of both of these problems shortly into therapy. There are only 3 failures to treatment. 1 patient with post-traumatic syncope of unknown aetiology who is nitrite sensitive continued with these episodes, and one such episode is brought on by 3 minutes of a Nitrodur patch being applied. She eventually responds to maintenance treatment with p.o. hydralazine in doses high enough to treat the vasospasm. The second patient is unable to tolerate Nitroglycerine or short-acting nifedipine, which caused angina, but did respond to Adalat, a long acting nifedipine preparation. The third continued on narcotics at low doses but unchanged from the dose she presented on.

Figure 2:
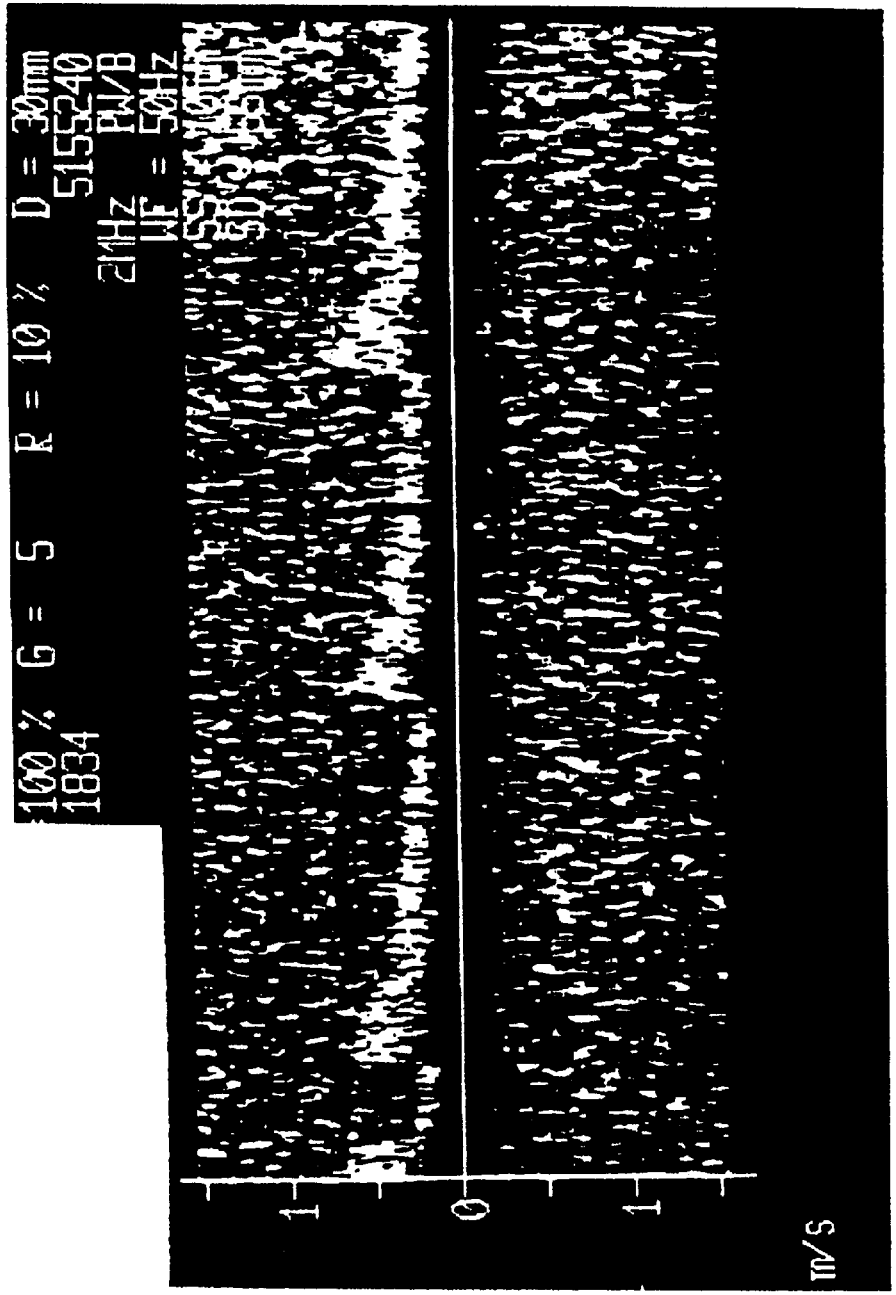
FIG. 2 is a TCD of MCA post Nitroglycerine spray obtained during continuous monitoring.
Figure 3:
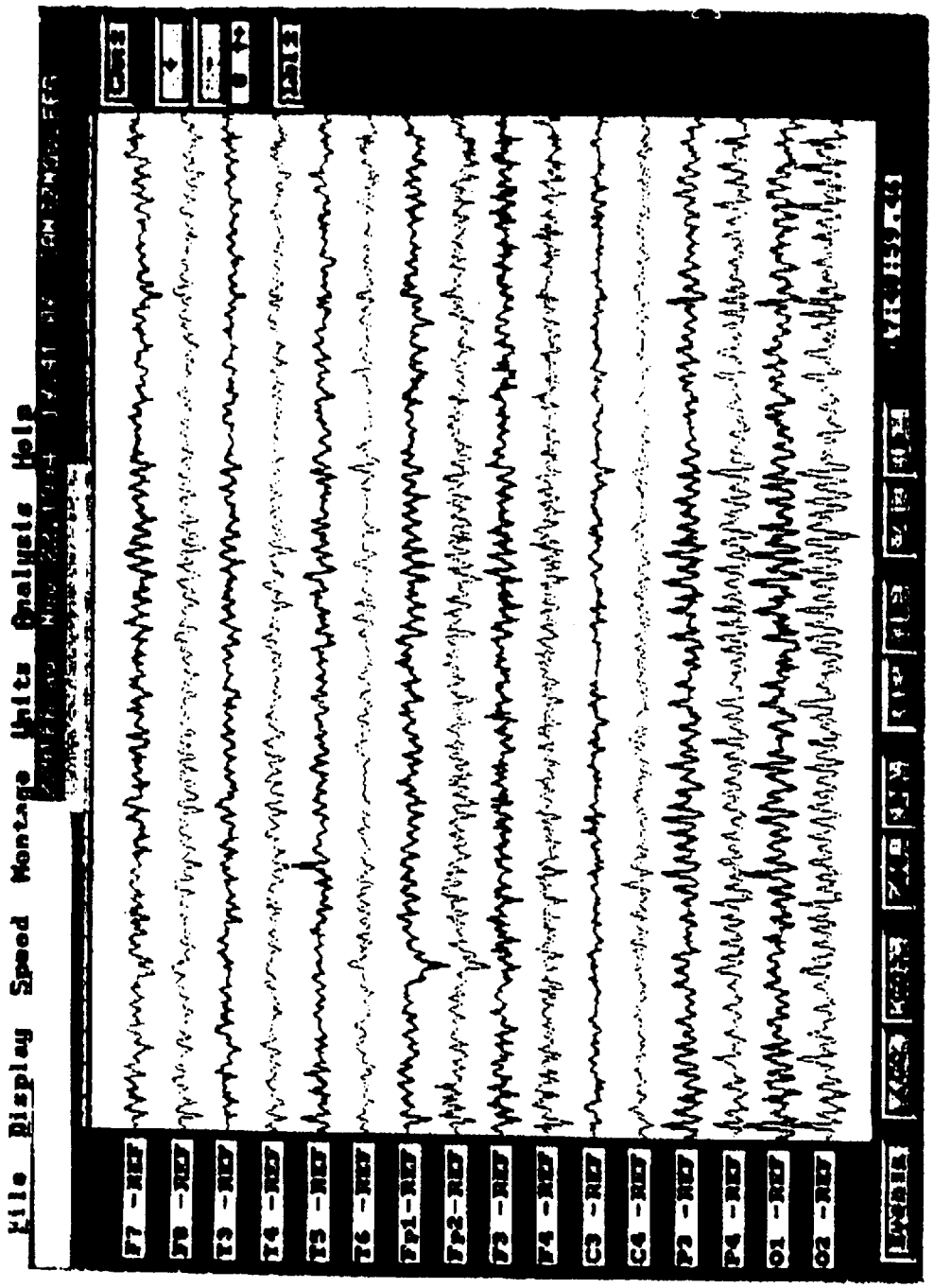
FIG. 3 is a related raw EEG scan.
Figure 4:
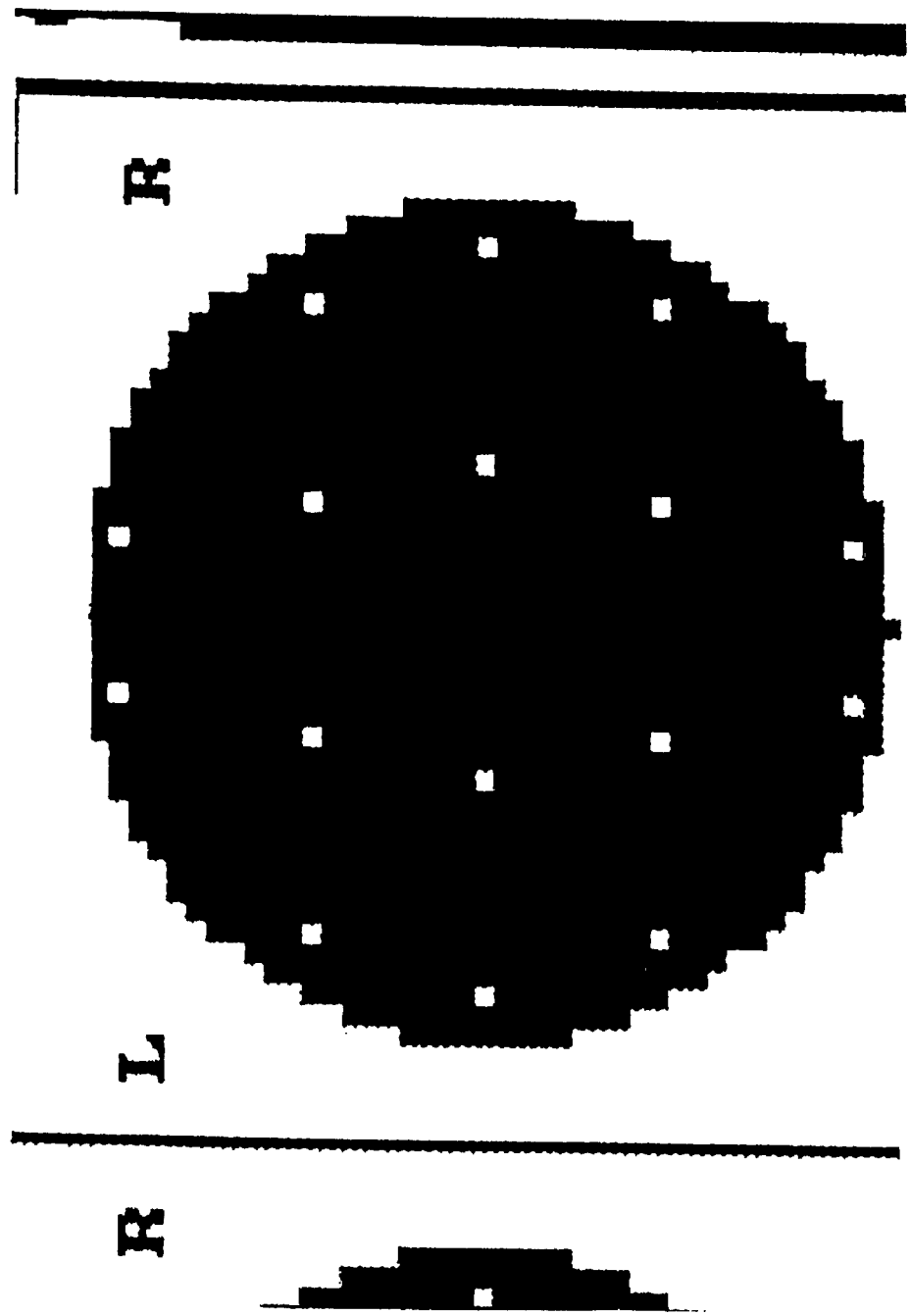
FIG. 4 is a brainmap showing a spatial distribution of alpha frequency mu rhythm.
Figure 5:
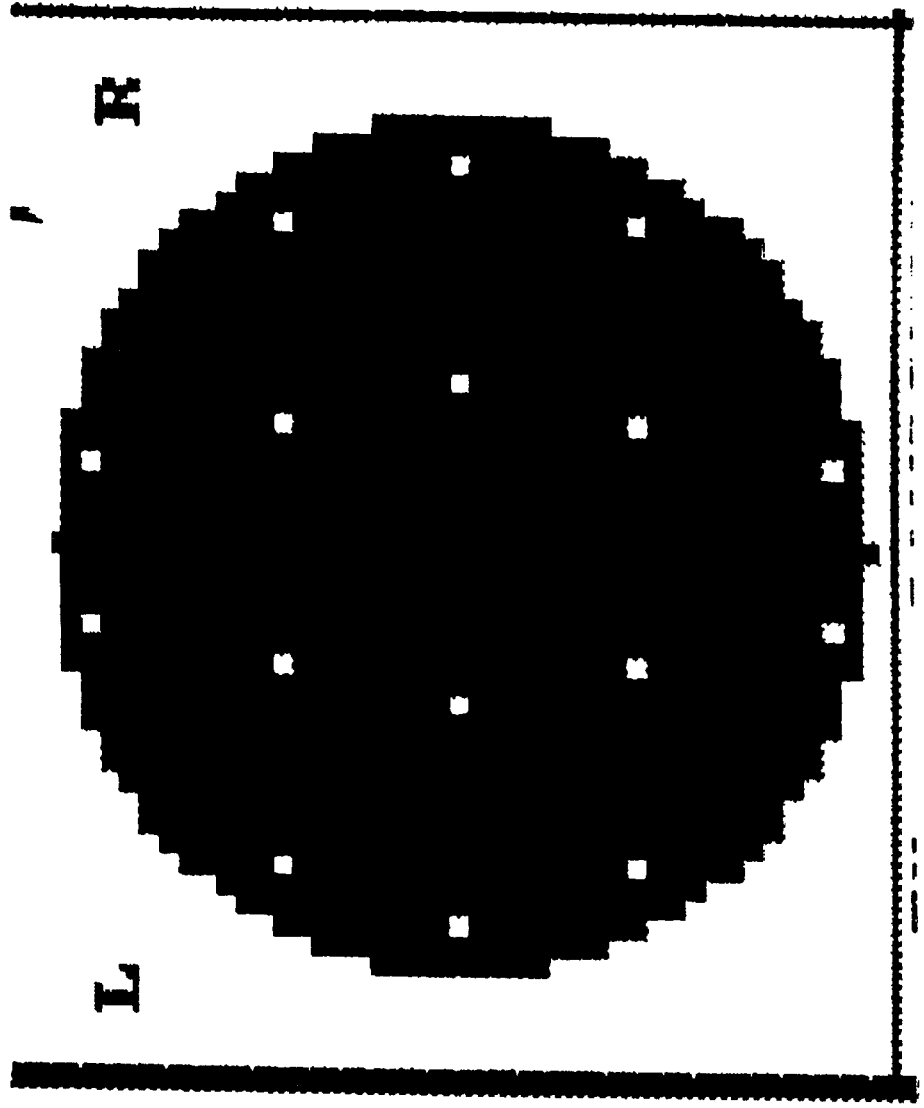
FIG. 5 is a brainmap showing a spatial distribution of beta frequency mu rhythm.

Applicant's patients range in age from 15–76, consisting of 12 men and 26 women. In four patients with post-traumatic fibromyalgia and fibromyositis, the symptoms of fibromyalgia and fibromyositis completely resolve while on Nitroglycerine. They are in the tapering phase, and the symptoms are not recurring of these fibromyositic and fibromyalgic conditions. The P300 in the 5 patients evaluated also shows improvement during the course of treatment. In 3 of these patients, this improvement is independently confirmed by the neuropsychologists treating the patient. The other patients do not have ongoing neuropsychological follow-up. FIGS. 1 and 2 represent examples of the baseline TCD while patient is symptomatic, and a follow-up TCD with resolution of patient's complaints after a Nitroglycerine sublingual spray. FIGS. 3, 4 & 5 represent examples of raw EEG tracing obtained on an average referential montage and two accompanying qEEG epochs. The first brainmap, FIG. 4, shows examples of the distribution of the alpha frequency mu rhythm, frontally, temporally, and occipitally; and the second, FIG. 5, is similar but shows that these mu rhythm frequencies are frequently in the beta range. On these maps, the frontal lobe is to the top, and the occipital lobe is inferior.

In 19 patients with MS-like syndrome and 1 with MS associated with breast implants, a similar pattern of complaints, Electro-encephalographic and TCD findings is seen. Our patients range in age from 23–61. The pattern of complaints is the same as the whiplash patients. Headache, concentration and memory disturbances, visual blurring, intermittent focusing abnormalities, balance disturbances, ataxia, photophobia, and hyperacusis are complained of in all patients. The severity of the complaints, however, tends to be less than that of the whiplash patients, however, their complaints of memory and cognitive dysfunction and mood swings tend to be considered by the patient to be their most severe problem in all but the one case who is felt to have MS. Of the 10 patients who had MRI's performed, 2 had a few scattered UBO's consistent with small white matter infarcts, and one had large plaques consistent with MS on MRI and brain biopsy. All patients had fibromyalgia and fibromyositis.

All but one of the patients had MRI or surgical confirmation of implant rupture and in that one patient, it is clinically suspected due to patient's symptoms, their progression, and length of time of implant (20 years). All patients had the same constellation of EEG and qEEG abnormalities, TCD abnormalities that paralleled the vascular distribution of the EEG changes in a fashion identical to that seen in the whiplash patients and that followed clinical distributions subserved by vasculature.

11 patients decided to start treatment with vasoactive medications. 10 started initially with IM Toradol, followed by maintenance dosing of Toradol given by mouth is seen to give consistent improvement clinically and with respect to the TCD. Unfortunately, gastritis developed in all cases and the patients are switched to Nitroglycerine by spray and patch, and is joined by the 11th patient, who initiated treatment with Nitroglycerine. Again, using the method outlined for initiating treatment with the MVA patients, baseline blood pressures, neuro exams, and TCD exams are performed with serial examinations on the first day also carried out as previously discussed. Results are identical. All patients have dramatic clinical improvement in exam and clinical symptoms with resolution of vasospasm as documented on TCD. All patients relapse as the initial dose of medication wears off as again documented by TCD. Although no patients are found to be nitrite sensitive in this group of patients, the TCD again became invaluable in monitoring and modifying dosage regimens. Interestingly, unlike the whiplash related patients, most of whom are able to taper their use of the nitroglycerin use within three–four months of treatment initiation without requiring the use of other medications, none of the breast implant cases have been able to dramatically reduce their need for the medication below a Nitrodur 0.1 mg patch for 4 hours a day. Again, the therapeutic window for Nitroglycerine modified in these patients over time, the TCD became again invaluable for individualizing the dose necessary for treatment. In all patients who started the Nitroglycerine treatment, the symptoms of fibromyalgia and fibromyositis resolved while on therapy and returned if they stopped therapy.

Five patients had a history of intermittent migraine headache, with only one patient noticing intermittently a history of scintillating scotoma as a prodrome to the headache. Later, after treatment had been initiated, all reported that they could start to recognize prodromes that they previously did not consider as prodromes. These included mild balance disturbance, feeling of a mildly clouded sensorium, or abrupt sensation of severe fatigue of acute onset. All 5 patients are men, ages 37–58. All showed evidence of vasospasm on TCD and the headache resolved with Nitroglycerine patches applied for 10 minutes to 1 hour. Follow-up TCD at the end of application of the patch are obtained in 3 patients which confirmed reduction of the vasospasm. At the time of symptomatic treatment, all patients had minimal lower extremity hyper-reflexia, and a minimally abnormal test on Rhomberg exam and tandem gait testing. These abnormalities all resolved with the nitroglycerin.

Discussion:

In applicant's practice, the association of cerebral vasospasm is consistently found to be associated with a typical clinical complex. This complex includes complaints of balance and memory problems, intermittent visual blurring, scotomas, or difficulty focusing, intermittent photophobia, and/or hyperacusis, memory and concentration lapses, word finding difficulties, dysaphasias; and, in more severe cases, headache which sometimes progresses to hemiplegic migraine with documentable weakness, asymmetric reflexic changes or fanning of toes or further progression to headache associated syncope or syncope with tonic/clonic activity and post-ictal confusion. Neurological exam most consistently shows a positive Rhomberg exam, abnormal tandem gait, and in more severe cases showed fanning of toes or intermittent Babinski's and reflex changes. The symptoms and neurological exam wax and wane in severity of abnormalities. In whiplash patients, the exam worsens with psychological stress or pain, and, in the breast implant patients, psychological stress would precipitate a worsening of the exam. The patients often appeared to be photophobic or would startle easily to sound. EEG and qEEG's, even those with syncope or syncope and secondary, observed, tonic/clonic activity, would be minimally abnormal. However, the pattern of EEG abnormalities, as well as the subjective complaints and neurological exam findings, mirrored the vascular distribution of the abnormalities seen on TCD. Interestingly, this syndrome in the whiplash patient and the breast implant patient has now been found to only rarely develop immediately with the causative trauma, but instead to develop over a time course of weeks to many months after the initiating irritant.

In the early stages of treatment of these patients, applicant monitors specific vessels continuously while giving patients test doses of medication. applicant did this in order to more quickly evaluate which medications are most effective for each patient and to individualize doses. It became clear that such extensive and time-consuming studies are not necessary, as this condition of cerebral vasospasm in these patients is a generalized phenomenon to the cerebral circulation. The problem is probably systematically generalized as common associated complaints during times of these previously mentioned complaints include prinz-metal type angina, intermittent coolness of the extremities to the touch, and menstrual cycle irregularities in some women. All of these symptoms, except for the menstrual cycle irregularities would be aggravated by stress and are improved by treatment with the vasoactive drugs. BAER studies are initially performed on many patients as part of the evaluation of the ataxia, but are not helpful as they frequently are abnormal if vertebral artery spasm is seen on TCD. The BAER abnormalities resolved with resolution of the TCD spasms in those where applicant has had the opportunity to repeat the study. Significantly, though, those with abnormal BAER's at institution of therapy, had more severe reactions to the initial stages of treatment with Nitroglycerine and reported more severe reactions when they had previously been treated with vaso-constrictive medications for headache control. It has now been found that Nitroglycerine, in the early stages of administration, can give transient severe vasoconstrictive episodes, apparently due to a hypersensitivity reaction in which, during early administration of the drug, some individuals develop transient worsening of the vasospasm which may result clinically in migraine headache, seizure, or syncope. In some cases, such episodes can be mistaken for stroke.

Thus, great care must be used in administering this drug to someone in the midst of an exacerbation. In applicant's practice, the first dose of Nitroglycerine is always given under direct physician observation, immediately after obtaining a baseline TCD. This is done as those patients with the most severe reactions to Nitroglycerine generally, but not invariably, had the most severe abnormalities on TCD, or are patients severely symptomatic for a long time, or are less than the age of 20. This transient supersensitivity may be witnessed on TCD but did not occur with any of the other vasodilating medications applicant has tried, specifically, p.o. clonidine, Dynacirc (isradipine), hydralazine, or long acting nifedipine. It, clinically, probably does occur in some patients after administration of the short acting form of nifedipine but applicant has not personally witnessed the TCD reactions for this drug as applicant has with the other mentioned drugs.

Multiple other vasoactive medications are tried on these patients prior to attempting nitroglycerin. Those medications that caused vasoconstriction on the TCD, such as Stadol (butorphanol tartrate), DHE, and Imitrex, in every case worsened the patient's neurological exam and mentation but improved their headache. However, in applicant's patients, the more serious neurological events such as syncope, TIA, or seizures, are usually preceded by a headache. Due to applicant's concern that headaches may be a significant warning sign of impending serious neurological events, the cerebral equivalent of angina, applicant attempted vasodilator to reduce the vasospasm. Those that resulted in vascular dilatation, such as Toradol, Nitroglycerine, clonidine, hydralazine, Dynacirc, and long acting forms of nifedipine, all resulted in clinical and neurological exam improvement mirroring the TCD exam's improvement. These medications also alleviated or treated the headache. All medications in this and generally reduce pulmonary capillary wedge pressure, which empirically defines a class of useful medications.

Common clinical symptoms of headache, intermittent visual abnormalities, ataxia or balance troubles in patients with usually normal brain CT or MRI scans but abnormal EEG and TCD findings suggestive of cerebral vasospasm are presented. These patients are found to have a clinical aggravation of their symptoms directly related to the degree of vasospasm seen on TCD. Techniques which modified this vasospasm could cause clinical improvement or worsening paralleling the degree of severity seen on TCD. This application is not meant as a final recipe for the treatment of cerebral vasospasm on the outpatient basis, but instead is meant to provide basis for further study into the mechanism of these findings in disparate conditions and possibilities for treatment.

Applicant believes he is the first to identify vasospasm in patients with the condition whiplash. Half of these patients are also identified as having either closed head injury symptoms or post-concussion syndrome symptoms. These patients have neuropsychological testings which for the most part confirmed the findings of closed head injury in the previously mentioned half of the group.

In treatment of patients with migraine headache, the present state of the art is to treat patients with migraine with vasoconstricting medications as opposed to vasodilation medications, and in fact the present state of treatment of these conditions with the vasodilating medications mentioned is considered that the vasodilator may cause migraine headaches. Additionally, applicant has four patients with attention deficit disorder and four patients with seizure, all with vasospasm and all of which have responded well seen from both neuropsychological testing or seizure control with the use of vasodilator as described herein. In summary, vasospasm has been discovered to be a clinically common and treatable entity.

In FDA attachments for medications in which migraine headache is identified as a side effect, no indications for the previously mentioned treatments are identified.

Additionally, good results are obtained in a number or patients presenting with systemic disorders, including cases of fibromyalgia, cardiac disease and even gastric disorders, by testing and treatment to reduce or eliminate vasospasms according to the techniques described above. Still further study after the filing of the provisional application shows good results in the treatment of additional diseases which have now been found unexpectedly to involve a substantial degree of vasospasm, comprising hyperactivity and Attention Deficit Disorder, deficits resulting from strokes of various causes, migraine, seizures, balance disorders, concussion, post-concussion syndrome sometimes including temporal mandible joint pain (TMJ) or facial pain, cerebral ischemia and other vascular components discovered to be associated symptoms in some cases of psychiatric disorders such as chronic depression and some psychosis. For brevity Appendix A (based on papers to be published) gives clinical details and the following Examples summarize the clinical treatment and results.

While the diseases to which the new techniques have been found applicable seem to be disparate and unconnected, the modality bridging all of them appears to be the relaxation of smooth muscle tissue by treatment with low dosage of vasodilator and the titration of this dosage over time to avoid overdosage as the patient's response to the medication changes. Thus, relaxation of smooth muscles underlying the vascular system alleviates vasospasm, the relaxation of spincter muscles alleveates BPH, and the relaxation of downstream arteries alleviates the effect even of physical buildup of cholesterol.

EXAMPLE

Attention Deficit Disorder

Attention Deficit Disorder has been found to affect more than 12 percent of the school age population. This disorder has now been found to continue into adulthood and many ADD adults with a mild condition had proceeded through life undetected. Limited blood flow to the brain (cranial perfusion) has been postulated as a cause for this condition. Two adults, siblings, were evaluated and treated as taught herein,(a regimen was made up of a low dose Calcium Channel Blocker, and an ACE inhibitor along with low dose Nitroglycerine and a Clonidine patch), to increase blood flow to the brain with results showing increased social and emotional control of themselves and IQ improvement of approximately 30 points. Also they improved in achievement motivation and specific goals for their lives.

EXAMPLE

Concussion or Post-Concussion Syndrome

It was discovered that most patients referred to a neurologist's office for brain injury or concussion do not have a brain injury. Rather, they have an injury to the control mechanism that controls blood flow to the brain. This injury results in causing blood flow to the brain to decrease. This drop off in blood flow accounts for all or much of the clinical symptoms. It is reversible. Of 22 patients randomly identified by computer with presenting symptoms of brain injury and a diagnosis of concussion, one third had no brain injury, but only a vascular disorder, and the other two thirds identified that a significant portion, or all of their symptoms were alleviated with the use of common vasodilating medication. A further aspect was that 22 out of 22 patients referred for evaluation of closed head injury and concussion complained, on careful questioning, of their symptoms becoming worse as time went on. These symptoms that developed or worsened progressively were reversed with vasodilating medication.

EXAMPLE

Psychosis Caused by Cerebral Ischemia

In this Example, a patient who has an acute psychotic break is presented. The patient is identified as having a history of migraines and then developing acute schizophrenia. She is hospitalized for an acute psychotic break. Due to difficulty in controlling the thought disorder, the hospitalization is extended for 3 weeks. She is then released and self-discontinued her medications. Out-patient evaluation of her reveals that the blood vessels leading into her brain are overly constricted, and she is placed on medication to dilate these blood vessels. The patient's thought disorder processes, memory disturbances and headaches completely resolve. This represents a new approach to the diagnosis and treatment of psychosis and underlying concerns.

EXAMPLE

Reversing Stroke Using Common Vasodilators

In this Example, three patients with strokes improved dramatically in minutes to days after devastating strokes by using the new therapy taught herein (e.g. Dynacirc 10 mg t.i.d. and repetitive uses of Nitroglycerin.) The first patient developed a large stroke, which caused her to be able to walk only with assistance and a cane, and not to be able to speak her thoughts. One month later, no major clinical changes had occurred. Within 45 minutes of instituting the present therapy, she can walk unassisted, speak normally and had only minimal weakness. By the next day, she can transfer from a dock to a boat unassisted. The second patient has been paralyzed for one year on his left side. Within one month, he has regained 80% of his strength throughout most of his body. Within four months he can lift 300 pounds with his paralyzed leg and 120 pounds with his previously paralyzed arm. The third patient has severe weakness in his right arm and face for four days. Within one hour of starting treatment, he has regained most of the use of his arm. Nitroglycerin and other medications all result in improvement in the patient's headache, but also resulted in improvement of any other neurological abnormalities including balance disorders, gait disorders, hemiparesis, abnormal Babinski's and abnormal reflexes.

Modifications

Specific compositions, methods, or embodiments discussed are intended to be only illustrative of the invention disclosed by this specification. Variation on these compositions, methods, or embodiments are readily apparent to a person of skill in the art based upon the teachings of this specification and are therefore intended to be included as part of the inventions disclosed herein.

For example, the vasodilators include many that are not named here, the tests for vasospasm are constantly improving and it will be evident that new tests for blood flow and others not named here will be useful in the step of testing for vasospasm described in this application and that the treatable diseases will expand as vasospasm is found to be a component of additional diseases. Reference to documents made in the specification is intended to result in such patents or literature being expressly incorporated herein by reference.

Appendix A

EXAMPLE

ADD

Method:

Two individuals were referred for Career Evaluations by their Mother because they lacked ambition and success in work. They were a 27 year old female and her 25 year old brother. They shared the same biological parents, both professionals, and shared similar behavior characteristics of:

Completing Junior College in 4+years.

No record of full time employment for 4 months or longer.

Limited friendships.

No specific career plans.

Enthusiastic beginnings but poor or incomplete endings.

Underachievement in relation to ability.

Both were administered a battery of tests which measured neuropsychological functioning and personality variables. The similarities continued with both scoring in the superior range on a non-verbal abstract thinking intelligence test; average on the Vocabulary subtest of the Wechsler Adult Intelligence Scale-Revised: average in fine motor coordination and organization.

Both scored low on achievement motivation, affiliation and the ability to ask for assistance when they had no solution to a problem. They were high on aggression and needed control.

On referral for neurological evaluation, mild physical and significant objective testing abnormalities were found. Both patients exhibited very mild balance difficulties only identified on careful neurological testing. The patients had a mild tendency to sway when standing at attention with their eyes closed (abnormal Rhomberg testing). Both, further, had difficulty performing a Tandem Gait with complete ease. The physical exam was otherwise normal. An EEG and computerized EEG were performed and were abnormal. These tests showed a frontal and temporal spatially distributed alpha rhythm on an average referential montage. Transcranial Doppler ultrasound showed middle cerebral artery velocities of greater than 0.8 meters/second bilaterally in the female, and 0.73 meters/second in the right MCA of the male, with a normal 0.26 meters/second in the left MCA. Interestingly, on a separate day, the male was retested and found to have elevated MCA flow velocities of 0.86 meters/second on the right, and 0.92 meters/second on the left.

EXAMPLE ADD

Treatment:

Both individuals were treated with vasodilating medications for 10 months and received psychotherapy and vocational counseling. Relaxation and hypnotherapy were also used to develop visualization skills for both recall of successful social and work experiences and to visualize successful outcomes of activities to do.

In serial testing, the male underwent TCD's on three separate occasions on the same day. After repetitive applications of Nitroglycerin, the patient was re-examined and underwent self-assessment, and had repeat Transcranial Dopplers performed. As the right MCA mean flow velocity decreased from 0.86 meters/second to 0.79 meters/second, to 0.72 meters/second, and the left MCA mean flow velocity decreased from a baseline of 0.92 meters/second, to 0.84 meters/second, to 0.79 meters/second, the patient's exam progressively normalized with eventual development of completely normal balance testing. The patient also identified significant improvement in concentration. By the end of the day, he identified that he could read, understand and retain news articles and magazine articles. He could also follow a television show throughout. He could do neither at the beginning of the day. Observers also felt his comprehension had significantly changed.

On the basis of the objective disorders of flow and the patient's reported and observed improvement during the trial episode of administering medications to decrease the observed vasospasm, we started the brother on vasodilators. After the patient had been on medication for approximately 3 months, the sister's observations of significant improvement in her brother's functioning resulted in her self-referring for evaluation and treatment. We initially used Nitroglycerin and later added a variety of Angiotensin Converting Enzyme inhibitors, Calcium Channel blockers, and Clonidine until the regimen that the patient best tolerated was found. This regimen was made up of a low dose Calcium Channel Blocker, and an ACE inhibitor along with low dose Nitroglycerine and a Clonidine patch.

Over the next 6 months, both sibling's neurological exams normalized. The Transcranial Doppler results showed marginal improvement from office visit to office visit. However, the patients have identified significant functional improvement which wears off in direct relationship to the vascular pharmacokinetics of the specific medication used.

EXAMPLE ADD

Results:

Both the male and female subjects experienced social, emotional, physical and intellectual gains through these treatments. Their Verbal IQ scores increased from scores of 110 and 119 to 143 and 146 respectively. On the Bender Gestalt Test they eliminated all errors and their drawings were better organized with improved fine-motor coordination. Both have been planning a continuation of their college education with specific goals in mind. The young man had played tennis in high school and has maintained playing recreationally. He had noted specific improvements in anticipating moves of his opponents and had improved his game significantly. This was also noted by his opponents and fellow tennis teacher.

Their personalities changed significantly. The female became less fearful and argumentative and was self assured. The male as stated "I can relate to friends and I am not the last to get the joke. I am less the point of jokes and teasing." These were significant personality and social changes for these individuals.

EXAMPLE ADD

Discussion of Possible Theory:

This study utilized siblings who had been considered OK in life, but themselves were frustrated and had self thoughts of failure. Based on Career Neuropsychological testing, they were found to be Adult-ADD. After 10 months of treatment with vasodilating medications and psychotherapy. they have improved their cognitive, social and emotional functioning.

Their gains have been significant and have stabilized. These have remained consistent for over 11 months and indicate a permanent solution.

From a neurological viewpoint, serial monitoring identified close relationship between functional abilities and a degree of vasospasm or constriction of the arteries. These patients' long term TCD's do not reflect major improvements in the resolution of the degree of spasm. The lack of complete resolution of the vasospasm probably relates to, in these two specific patients, their inability to tolerate even moderate levels of vasodilators without developing symptomatic hypotension. These two patients share in common with all Applicant's patients referred for idiopathic Attention Deficit Disorder that we can seldom completely resolve the vasospasm identified on ultrasound, but that any improvement in the arterial constriction parallels functional improvement. Patients with secondary Attention Deficit Disorder-like syndromes, such as are seen after trauma, closed head injury, neck injury, Reflex Sympathetic Dystrophy, cerebrovascular accident, silicon implant disease and other toxic vasculopathies, and so on, generally have profound vascular relaxation with the commonly used vasodilators after approximately 6–10 months of treatment. Nonetheless, our therapy in these two patients has probably been successful by causing vasodilation of the small arterioles and other blood vessels in the brain. Such vasodilation would decrease the ischemia of the brain tissue and improve performance. On a day when serial testing was performed when repetitive vasodilation medication doses were used to decrease the vasospasm, the patient showed significant improvement. This argues that improved control of the vasospasm may be expected to cause further functional improvement. Equally, it is strongly recommended that psychological counseling and biofeedback be utilized in the long term treatment of these patients, as such treatment, by decreasing autonomic nervous tone, also enhances vasodilation.

EXAMPLE ADD

Literature

Learning disabilities (LD) and attention deficit hyperactivity disorder (ADD) represent almost 25% of school age learning—conduct problems. Despite their prevalence, much confusion exists over the differentiation between LD and ADD. This confusion emanates from the fact that some individuals suffer from both disorders and school systems tend to group both disorders in the same classroom or diagnostic category. The major confusion results from the failure to appreciate the considerable progress that has been made in recent years in defining and classifying each of these common neurocognitive and neurobehavioral problems (Shaywitz, et.al., 1995, p.s50).

Hallowell & Ratey. 1994 have found that a large number of adult patients viewed as depressed, anxious, obsessivecompulsive, personality disordered, dissociative or prone to substance abuse were ADD. Until recently mental health professionals have not paid much attention to this disorder in adults, despite the fact that attentional disorders have major ramifications for intellectual, cognitive and emotional experience. Miller, in a Wall Street Journal article in 1993. identified the following as symptoms of ADD in adults:

A short attention span, especially for low-interest activities.
Enthusiastic beginnings but poor endings.
Low frustration tolerance.
Difficulty listening.
Argumentative.
Frequent job changes.
Underachievement in relation to ability.
Frequent and unpredictable mood swings.
Avoids group activities; a loner.
Spends excessive time at work because of inefficiency.

EXAMPLE ADD

Bibliography

Hallowell, Edward M. and Ratey, John J. *Answers to Distraction*, Pantheon Books, New York. 1994. p. 207–211.

Shaywitz, Bennett A., Fletcher, Jack M. and Shaywitz, Sally E., "Defining and Classifying Learning Disabilities and Attention-Deficit/Hyperactivity Disorder.", *Journal of Child Neurology*, Vol. 10 Supplement Number 1, Jan., 1995.

Concussion or Post-Concussion Syndrome

Professional Abstract

This article represents the first discussion that concussion and post-concussion symptoms as well as progressive deterioration after an accident may be vascularly mediated. Progressive deterioration of patients, as well as patients complaining of concussion or post-concussion syndrome or closed head injury, should include vascular ultrasound screening of the brain.

This paper represents a complete evaluation of twenty-two patients referred for evaluation of concussion and post-concussion syndrome. All patients on referral from their primary treating physician or psychologist also carried the diagnosis of concussion. All patients complained of progressive deterioration starting some time after an accident.

Six of 22 patients had a loss of consciousness, 7 of 22 patients had altered mental status at the time of the accident which cleared completely, and 9 of 22 patients had no concussion or mental symptoms; only spinal symptoms (2 of these 9 did have a headache). It is assumed that one third of the patients did not have a brain injury at the time of impact. An additional one third had complete resolution of all symptoms after the trauma. However, by the time of presentation, all had an abnormal neurological exam and symptoms of concussion, closed head injury and post-concussion syndrome.

All patients were found to have vascular flow abnormalities by the Transcranial Doppler (TCD) showing evidence of abnormal constriction of the arteries intracranially. Other imaging modalities of these patients included CT and/or MRI scan in all patients, EEG and computerized EEG in all patients: SPECT scan and neuropsychological testing were additionally added in many patients. The comparison of these various imaging and diagnostic modalities is made.

EXAMPLE

Concussion or Post-Concussion Syndrome

Comparative Analysis and Evaluation

Twenty-four patients having been computer coded as concussion syndrome were chosen at random per data from the office computer; the patients were seen in this office between Feb. 23, 1995 through January 1996. Two of the patients were miscoded and were dropped from this study. All patients were referred by their primary physician or psychologist with the diagnosis of concussion. Injuries of twenty patients were sustained by motor vehicle accidents and two patients' injuries were a result of falling. Each patient was given a neurological examination by a board certified neurologist, Transcranial Dopplers, standard and quantitative EEGs, and most were given either/or MRIs or CT scans of the brain, neuropsychological testing, and three patients had SPECT Scans of the brain.

EXAMPLE

Concussion or Post-Concussion Syndrome
Clinical Presenting Symptoms:

Loss of consciousness varied with patients having very brief black-outs of seconds to twenty-five minutes. Six patients had a loss of consciousness at the time of the accident with four patients unconscious for brief seconds, one patient for five minutes and one patient about twenty four hours. (Ref.Table IA. Period of Total Unconsciousness at Scene of Accident with Other Related Symptoms)

There were seven patients that denied loss of consciousness but had less severe altered mental status such as amnesia, mental confusion, dazed, dizziness, vertiginous and/or ataxia. (Ref.Table IB. Altered Mental Status With No Unconsciousness and Related Symptoms)

A third class of patients consisted of nine patients who had no altered mental status but experienced a combination of a variety of symptoms such as neck and back pain (two of them also had a headache). One patient had no symptoms at all at the time of the accident but developed severe back pain later at night following the accident. (Ref. Table IC. Physical Symptoms With No Altered Mental Status.)

Table IA. Period of Unconsciousness at Scene of Accident and Other Related Symptoms
of Patients Period of Total Unconsciousness & Related Symptoms
4 Brief loss of consciousness with neck and back pain of seconds to less than 5 minutes
1 Loss of consciousness for 5 minutes, dazed, confused with neck and back pain
1 Loss of consciousness for about 24 hours & awoke with neck and back pain
Table IB. Altered Mental Status with Related Symptoms but No Total Unconsciousness
3 Immediate severe headaches, confusion, neck and back pain
1 Neck and back pain, vertiginous and nausea
3 Amnesic for accident, confusion, back and neck pain
Table IC: Physical Symptoms with No Alter Mental Status
2 TMJ and neck pain
1 Neck pain only
3 Neck and back pain
2 Headaches and severe neck pain
1 No symptoms at all at time of accident but later that night developed back pain.

EXAMPLE

Concussion or Post-Concussion Syndrome
Additional Physical Symptoms:
Temporomandibular Joint Injury An associated finding in this study was TMJ and facial pain. Of the twenty-two patients studied fifteen patients had pain in the temporal mandibular joints with ten of the patients diagnosed with having TMJ and five patients with mild symptoms of popping of TMJ was considered to be clinically insignificant. Onset of symptoms varied from immediate discomfort to four months post the accident. Some of patients that were later diagnosed as having TMJ related that in the beginning, they had so much head and facial pain that they were not able to determine where the pain was coming from until they have had a chance for some of the injuries to heal. (Ref. Table ID. Time of Onset of TMJ Symptoms Following Accident)

Table 1D. Time of Onset of TMJ Symptoms Following Accident
5 patients don't know when pain was localized to TMJ
2 patients had immediate pain in TMJ
1 patient had pain about two hours later
3 patients had pain not immediately but within twenty-four hours of trauma
1 patient with previous treated TMJ became worse within twenty-four hours following new injury
3 patients' pain was localized to TMJ 2 months post accident

EXAMPLE Concussion or Post-Concussion Syndrome

Thoracic Outlet Syndrome:

A common associated complaint was symptoms of upper extremity intermittent paresthesias consistent with Thoracic Outlet Syndrome. Only rarely debilitating, and not complained of by the patient unless checked for during a Review of Systems of 22 patients. (Ref. Table 1E.).
Table 1E.
19 had Thoracic Outlet Syndrome.
3 had no symptoms of Thoracic Outlet Syndrome.
Interval Between Date of Injury and Presentation:

Time lapse between the date of injury and the patient's initial office visit varied from two weeks post accident to years.
(Ref. Table II, Time Lapse from Date of Accident & Initial Office Visit)
Table II, Time Lapse from Date of Accident & Initial Office Visit
# of Patients Lapse time injury and initial office visit
1 11 days post accident
3 1 month
2 2 months
4 3 months
1 4 months
1 5 months
3 6 months
1 7 months
1 8 months
1 14 months
1 16 months
2 3 years
1 25 years
Previous History of Head Injury:

An interesting finding during this survey was that 50% of the patients have had at least one previous accident.(Ref. Table III. Previous History of Head injury. Two of these patients had loss of consciousness, one for less than 24 hours and the other patient, with a Glasgow Score of 4, was unconscious for three months. (Ref. Table III, Previous History of Head Injury)
Table III. Previous History of Head Injury
13 patients had never had a previous accident
4 have had 1 previous accident
2 have had 2 previous accidents
3 have had 3 previous accidents

EXAMPLE

Concussion or Post-Concussion Syndrome
Clinical Presenting Symptoms Summary

All patients developed delayed and progressive symptoms which consisted of as neck and shoulder spasms migraine headaches, memory and concentration problems, easy distractibility in an attention deficit-like disorder, and most complained of intermittent upper and/or lower extremity paresthesias due to associated spinal injuries. Most patients complained of intermittent balance problems of varying, usually mild severity, tinnitus and/or visual blurring were also frequent complaints.

EXAMPLE Concussion or Post-Concussion Syndrome

Testing Results:

The patients were evaluated using multi-modality neuro-diagnostic and imaging techniques. vaso A discussion of MRI, SPECT scan results, neuropsychological testing, Transcranial Doppler, EEG and QEEG follows. All modalities proved to be of value.

EEG and QEEG Results:

With respect to EEG's, correlation of the abnormalities seen in the standard and quantitative EEGs are very close in some cases, but in other cases abnormalities are seen in the standard EEG that are not seen in the qualitative EEGs and vice versa. The most common feature observed in the standard EEG being an alpha-like rhythm occurring bilaterally in the frontal and temporal areas that was disassociated from the posterior alpha band seen only on an average referential montage. The quantitative EEG's most common finding was an underlying-slowing in the theta and/or delta frequency range located bilaterally in the frontal and temporal areas and at times appearing in the posterior head regions. Epileptogenic spike discharges obvious in both standard and quantitative but not in the averaged EEG. However, the QEEG aided in localization of the discharges with further analysis. (Ref. Table IV, Comparison of Findings of Standard and Qualitative EEGs)

Table IV. Comparison of Findings of Standard and Quantitative EEGs:

A. Summation of Standard and Quantitative EEG Findings:

18 Patients had abnormal standard and quantitative EEGs
4 Patients had normal standard and quantitative EEGs
2 Patients had epileptogenic spike discharges obvious in both standard and quantitative EEGs but not in the average EEG.

EXAMPLE

Psychosis Caused by Cerebral Ischemia

Professional Abstract;

A patient with a schizophrenic reaction after a long history of migraines is presented. The patient was hospitalized for an acute psychotic break. Due to difficulty with regulating the thought disorder, the hospitalization was extended to 3 weeks. On discharge, the patient self-discontinued her medications with a return of headaches and thought disorders. Evaluation of her including EEG and vascular evaluation of the brain showed abnormalities. The patient was placed on medication to treat the vascular constrictive disorder and the patient's thought processes returned to normal and the patient became headache free.

Case Study

The patient presented with a long history of migraine headaches which had progressed over the year prior to development of her schizophrenic break. The headaches would become daily. The patient noted at times, due to the headaches, she would have intermittent degrees of confusion, disorientation or memory disturbances. She had no history of seizures. Two months prior to presentation she became increasingly distressed about personal family issues with aggravation of the headaches. She treated herself with over-the-counter medications and then became concerned that her husband might be leaving her. She went down to meet him at his place at work, but became confused about how to enter the building, and decided he was probably trying to leave the state. She stole a truck, drove along the road she thought would lead to him. She was followed by police who identified her as having disorientated thought processes. She was hospitalized for psychological evaluation, was found to have a reactive psychosis and schizophreniform disorder.

The patient continued to have hallucinations and delusions. was placed on Haldol (Haloperidol) from which she did not respond. Headache was not a significant complaint in the hospital. She was eventually placed on a combination of Navanne (Thiothixene) and Ativan (Lorazepam). She improved significantly. Blood work including thyroid studies were normal. The patient was released and continued to have severe headaches, concentration problems and memory problems. She felt these problems were aggravated by activity. Her neurological examination was normal, A CT scan of the brain was obtained which was normal. An EEG and a QEEG showed intermittent left temporal spike discharges, as well as bifrontal temporal slowing activity in the 5 mv range in the delta and theta patterns. A frontal alpha frequency band was also identified on an average referential montage as well as the computerized EEG. Transcranial Doppler Artery showed evidence of mean flow velocities in the MCAs bilaterally of 0.65 to 0.75 meters per second, and the basilar artery of 0.7 meters per second.

The patient was placed on Inderal (Propranolol) as well as Depakote (Sodium Valproate) without change in her EEG and continued flow abnormalities on Transcranial Doppler Artery. The patient was then placed on Nitroglycerin with complete resolution of her daily headaches and improvement in her middle cerebral artery flows to the normal range.

While taking Nitroglycerin medication, the TCDs continued to improve with MCAs approaching 0.37 meters per second to 0.5 meters per second. The patient's headaches completely resolved as did memory disturbances, concentration problems and emotional lability.

Discussion

The patient has a long history of migraine and develolped migraine and/or stress-induced schizophrenic reaction. She had poor response to Haldol (Haloperidol), but good response to Navane (Thiothixene). On presentation to the neurologist's office, the patient was off Navanne and evidence of vasospasm and evidence consistent with cerebral ischemia as well as the spike discharge was identified on EEG. The patient did not respond to standard antimigraine medication or seizure medication. The patient responded promptly to low-dose Nitroglycerin for control and management for migraines with no recurrent episodes of thought process disorders, memory disorders or disorientation when taking medication.

This suggests that some patients with vasospasm and vasoconstriction with secondary ischemia of the brain may develop neurocognitive changes including psychosis. Applicant has had several other patients with diagnoses of chronic depression or of steroid induced psychosis, in these cases headache was not a complaint, who had similar vasospasm identified on Transcranial Doppler and similar EEG changes as this patient. They also responded with clearing of their psychiatric disorders with vasodilators. It is thus our recommendation that, in the evaluation of the psychotic or psychiatric patient, evaluation for vasospasm and cerebral ischemia should be performed and treatment instituted empirically to reverse any abnormalities found, as the psychiatric disturbance may have a vascular component.

Migraine Forum (Whip-Lash/Breast Implants/Migraine)

Applicant has a baseline practice consisting of mainly post-traumatic, closed-head injuries and post-traumatic migraine disorders of which many have attention deficit disorders (ADD). However, several years ago Applicant had a large number of patients who presented with ADD of which the origin of their problems was associated with silicon breast implants (silicon toxicity). What became evident in evaluating of these patients was that the neuropsychological tests, computerized EEG and Transcranial Artery Doppler results were essentially identical. Another common characteristic in these patients was the waxing and waning nature of at least some of their complaints. Those patients with Attention Deficit Disorder both post-traumatic and in particularly those patients with silicon breast implant disease with MS-like syndrome would have normal neurological examination one day and on another day the exam would be normal. This finding substantiated the patients' complaints of waxing and waning of symptoms and seemed to be related to the degree of physiological or psychological stress the patient experienced when being interviewed or tested. The degree of abnormality of neurological exams would extend to the point of normal or abnormal Romberg and Tandem Gaits, reflex examinations and Babinski examinations in the same patient. Evoked potential test results varied from normal to abnormal on different days and the testing was performed by the same examiners.

In this same time frame, a series of new medications were developed to treat migraine headaches. As headache was a major complaint of many of Applicant's patients, we tried these medications out including Imitrex (Sumatriptan), IM Toradol (Ketoralac) and other medications under direct monitoring. As Applicant's patients tend to be intractable, it was not expected that any of these medications would have dramatic results. Rather, it was expected that one or another set of medications might help point the way into using specific classes of medications or approaches. Accordingly, each of these patients. equivalent of a large number of patients, were monitored continuously across the day. The patients would come in and be hooked up with EEG's or Brain Stem Auditory Evoked Responses, or VEP's, or Transcranial Dopplers, and across the day would have many of the different short-acting medications tried on them to see which would work and which monitoring tool would be most effective in identifying the improvement.

With respect to the different monitoring tools, some were more helpful than others. It was found that the EEG was not very sensitive. The Brain Stem Auditory Evoked Response and other evoked potential tests were very insensitive tools for monitoring, because of the length of time required to perform the test after short-acting medications were given in IM or sublingual or nasal spray administration route. The Transcranial Doppler consistently appeared to give the best indication as to which medications would work. If an ultrasound showed improvement, the patient invariably also reported improvement in their clinical symptoms. These symptoms included not only headache, but also sensations of confusion, balance disorder, abnormal Romberg or Tandem Gait or other neurological abnormalities. If the medications showed evidence of increasing vasoconstriction on the doppler, the patients who had a headache, frequently reported improvement in the headache, but a worsening of their confusional state or a worsening of other neurological symptoms. Those patients were identified as having improvement on ultrasound with doppler also showed resolution of their headache, but did not show the deterioration in their neurological effects. This was completely unexpected. The general approach towards migraine and headache has always been that the headache represents a vasodilation and frequently a hyperperfusion state. The aura, of course, represents a vasoconstrictive phase. What our results seemed to suggest was that the doppler, which looks at essentially the area of blood vessels around the base of the brain, was showing vasoconstriction. Vasoconstrictive medicines would relieve the headache presumably through a similar mechanism, as a vasoconstrictive medication probably relieved coronary artery disease. It would relieve it by decreasing the vasodilation that occurs downstream from the area we are able to directly insonate.

Unfortunately, if cerebral artery disease is anything like coronary artery disease, that downstream dilation represents an attempt by the body to compensate and maintain perfusion to thus becoming ischemic.

In Applicant's patient population all medications which resulted in vasoconstriction. relieved the headache, but caused neurological deterioration. As the medication wore off. as documented by the patient's clinical symptoms, sonography data, the patient's neurological abnormalities improved. Similarly, those medicines which resulted in direct vasodilation such as Hydralazine (Apresoline), Nitroglycerin and other medications all resulted in improvement in the patient's headache, but also resulted in improvement of any other neurological abnormalities including balance disorders, gait disorders. hemiparesis, abnormal Babinski's and abnormal reflexes.

Observations Noted Concerning Transcranial Dopplers

A special word about Transcranial Doppler needs to be made. We found that morphology of a Transcranial Doppler Artery Ultrasound is as important as mean flow velocities. In our patients, as they became more normal, and as their fixed deficits and europsychological abnormalities resolved etc., the morphology of the wave form would be similar to that of an internal carotid artery tracing. We did not find that there would be elevation of flow readings throughout diastole, as is more commonly published. It is important to identify that the original normative data obtained in 1979, used for "Normals" patients with post-traumatic migraine disorders, "psychogenic seizures", and the interictal migraine phase may not be appropriate. It is important to note that other labs which have done less extensive studies of normal versus non-normal, may have unknowingly used many patients with a history of migraines or whiplash headaches. Some have not identified the close relationship between degree of vasospasm and clinical abnormalities. This may be due to less lengthy monitoring or evaluations being carried out by those labs in comparison to our own. Equally, the trend clinical correlation is a general one. Remembering hemodynamics, it is important to note that if the blood vessel is constricted, patients do have a limited ability to compensate for the effects of that vasoconstriction by dilating distally to the constricted area.

Patients will not be abnormal clinically during the early stages of constriction of an artery. It is only once the downstream area is no longer able to dilate to a degree enough to maintain a significant pressure gradient across the vasoconstricted area that the patient will develop symptoms. It is important to continue to monitor and treat these patients until the sonographic studies return to normal and beyond. Realizing that blood vessels constrict across the day in response to sympathetic nervous system variability, internal steroid release, physiological and psychological stress, including the physiological stress of photic stimulation, driving etc., and thus to obtain an ultrasound at one moment, must be correlated with the patient's clinical symptoms and any complaints of variability across the day.

We also found that over time, chronic, untreated patient studies frequently falsely appear to normalize with a dropping of mean flow velocities. This occurs as the body develops compensating mechanisms to relieve the ischemia. Thus morphology becomes extremely important in identifying those who have ongoing vasoconstrictive disorder intracranially. The development of a pattern as time goes on is to have a blunted upstroke in the systolic portion of the ultrasound, but with an overall mean flow velocity of less than 0.6 meters per second. That blunting, which is also seen in disseminated vascular disease from any cause, is highly suspicious for severe vasospastic disorder. A computerized EEG or standard EEG consistent with brain dysfunction or ischemia, and/or neuropsych testing consistent with variability of cognitive injury (especially with fluctuating cognitive deficits across several hours or days of testing) with ischemia is often helpful corroborating study. These are patients who should not be treated initially with Nitroglycerin or other potent medications, but should first have other medications which are direct vasodilators instituted at low doses and slowly advanced as the patient is able to tolerate it. This institution with alternative vasodilators, tends to decrease the incidence of a potentially dangerous nitric oxide sensitivity reaction.

With respect to Nitroglycerin, what we have seen is several time courses of the effect of Nitroglycerin. The first is an acute effect which lasts between 15 and 45 minutes. The method of administration being a patch, pill or sublingual spray determines the rapidity of absorption and distribution. It seems to have a lingering effect for approximately 2 to 3 hours. Nitroglycerin then gets converted into a variety of subsidiary byproducts, all with some vasodilating properties. Each of these medications themselves can accumulate in patients to toxic doses, and can cause a reactive cerebral vasoconstriction. Thus, it is easier to maintain patients on intermittent low dose Nitroglycerin applications, then chronic applications of medication, as the clinical data and clinical response to the vasodilator challenge becomes confused. With respect to Nitric Oxide sensitivity, those patients in Applicant's clinical practice who have not been premedicated with a beta blocker, an alpha blocker or a direct vasodilator such as a calcium channel blocker or an ACE inhibitor, who are given their first dose of Nitric Oxide and developed acute erythema of the nose or face, are having a reactive vasoconstriction and distal vasodilation occurring at the same time. Those patients on Transcranial Doppler Artery Ultrasound will have acute spasm of the arteries and active constrictions and dilations may frequently be seen. Those patients may have a seizure or a stroke or a blackout spell. This problem can be immediately reversed with IM Toradol (ketoralac). Toradol in 90 to 120 mg IM doses causes acute vasodilation on ultrasound in most patients. In lower doses, the Transcranial Doppler Artery ultrasounds generally do not show significant changes, but the patient reports a symptomatic improvement. For most patients, standard doses of nitrates in any form will aggravate the vasospasm.

IV Toradol (Ketorolac) in 30 to 60 mg doses does not cause any improvement on Transcranial Doppler Artery Ultrasound, and patients generally report a sensation of vertebrogenic syndrome with increase spaciness, confusion, worsening headache and worsening spasm. Although Applicant has not identified this directly, their clinical course is that of a development of a vasoconstricted vertebral or basilar artery syndrome. This probably relates to a carrier drug in the I.V. Toradol solution, as giving the Toradol intramuscularly (I.M.) or in the alternative oral form after oral or I.M. loading gives the expected vasodilation. Without a change in formulation, Applicant would not recommend the I.V. use of Toradol to reverse acute and life threatening vasospasm or stroke. Multiple medications over the last several years have now been tried for the vasodilators. Each of these classes and results will be discussed in their specific following paragraphs.

With respect to beta blockers. Inderal (Propranolol), Tenormin (Atenolol), Normodyne (Labetolol), Lopressor (Metoprolol) have all been tried. None of these have been significantly effective at vasodilation. However, when using vasodilators, patients will frequently notice waxing and waning of their effectiveness. This is especially noticeable in patients who are beginning to be tapered off their medications due to good responses, and thus cannot tolerate higher doses of vasodilators without developing symptomatic lethargy, hypotension, etc. from the medications. In these patients. Beta blockers have been extremely effective in smoothing out the sympathetic nervous system excitability and variability that may be seen. In Applicant's patient population, Inderal (Propranolol) has been most effective. The other medications have not been effective, although probably are useful in blunting any acute response to Nitroglycerin administration from a hypersensitive Nitric Oxide response, if the patient is prone to such a response. Alpha blockers have been tried. Clonidine has been extremely effective. Hytrin (Terazosin), Ismelin (Guanethidine). Minipress (Prazosin), have been all tried, with less successful results. Cardura (Doxazosin) is still being tried, but initial results are just now coming available. Dibenzyline (Phenoxybenzamine) has also been tried, and appears to be relatively mild, similar in action on the vasospasm as Hytrin (Terazosin). Angiotensin Converting Enzyme Inhibitors (ACE) inhibitors have been tried including Accupril (Quinapril), Altace (Ramipril), Capoten(Captopril), Lotensin (Benazepril), Monopril (Fosinopril), Prinivil (Lisinopril), Zestril (Lisinopril timed released), Univasc (Moexipril), Vasotec (Elalapril), Cozaar (Losartan). Accupril (Quinapril) has consistently been the most effective.

With use of Accupril (Quinapril) and concomitant administration of low dose Nitroglycerin, 1/10th inch once a day to several times a day, most patients may be eventually weaned from the use of oral medications, although Applicant do tend to maintain them on low dose Nitroglycerin in perpetuity, as the inciting cause of the vasospasm usually remains and usually causes redevelopment of symptoms. However, these symptoms and radiological as well as symptomatic vasospasm may be controlled with low dose medication if Accupril (Quinapril) is used initially. The timed release medications such as Zestril (Lisinopril) are extremely effective in part due to increased patient compliance. Although Applicant personally finds these two aforementioned medications the most helpful, Capoten (Captoptil), Lotensin (Benzepril), Prinivil (Lisinopril) are close second tier medications. The other ACE inhibitors tend to be effective, but a third tier alternative drug. However, as a patient becomes intolerant to the stronger ACE inhibitors, these second and third tier drugs may be very helpful in preventing and controlling the vasospasm without developing intolerance to the medication. Similarly, in less severe cases, these are excellent first line drugs. Calcium channel blockers have been tried. In the most severe cases, Dynacirc (Isradapine) has been extremely effective. Adult (Nifedipine) in standard doses and timed release dosages has been helpful but as a second line drug. Careen (Nicardipine), Nimotop (Nimodopine), Cardizem (Diltiazem), Norvasc (Amlodipine) have been less effective in relieving the vasospasm or in allowing a degree of vascular relaxation sufficient to allow the patient to taper from the medication over time. Sular (Nisoldipine) and Plendil (Felodipine) appears to be slightly milder than Dynacirc (Isradapine) and has been effective in those that could not tolerate Dynacirc. Verapamil in its many manifestations is only rarely used, due to its minimal direct effect on vasodilating the vasculature as documented by Transcranial Doppler or in its ability to affect the outcome of these disorders. Vascor (Bepridil) is just now being tried on some patients. Of course, the general comments concerning ACE inhibitors also apply to these medicines. Appiicant's first line medications may be too strong for the other physicians' patient populations if those practices don't tend to attract as severely impaired individuals. Thus, the second and third tier medications may be better tolerated in less severely affected people, and similarly, as patients are able to taper from medications, they may taper into more mild medications from the same classes as previously were shown to be successful. Other Vasodilators that have not been previously discussed have also been tried. Hydralazine is effective, but tends to cause significant blood pressure changes in these patients.

Interestingly though, Hydralazine tends to improve the morphology of the diastolic flow component dramatically, which, in view of Hydralazine's effect on arterioles, bolsters the perspective that the diastolic phase of the Transcranial Doppler is a good indicator of downstream runoff. Flolan (Epoprostenol) has not yet been tried, nor has IV Papaverine or Inocor (Amrinone). Reserpine has been extensively used. It can be very effective. It's initial effect is parasympathomimetic. A later effect is sympatholytic. Its role is that it may be very effectively used as an adjunctive drug especially when patients have difficulty tolerating stronger vasodilators. The dose which initially is most effective of Reserpine frequently needs to be decreased dramatically (generally 50%) approximately 6 weeks into therapy as the sympatholytic activities start to become significant. Antipsychotic agents have also been used. Several of Applicant's patients who Applicant will be reporting on later, were psychotic, and responded well to these medications and had significant vasospasm identified on ultrasound which improved after the administration of medication. Of the antipsychotic. Mellaril (Thioridizine) has not been effective. Thorazine Chlorpromazine) has been moderately effective. Navane (Thiothixene) has been extremely effective, and Respiradol (Respiradone) has generally improved the patient's symptoms, but had no significant improvement on ultrasound. It has been less well-tolerated in comparison with Thorazine and Navane, interestingly enough, most of the patients who were placed on Navane, did not continue to require Navane two to three months after starting the medication, and were able to be weaned from that and had better response to their other vasodilators. In general, Navane was used as a first line drug in patients who had severe elevations of Transcranial Doppler Artery mean flow velocities greater than 1.3. and we would generally expect 50% improvement in the Transcranial Doppler Artery Ultrasound within a half hour of administering Navane by liquid solution. The solution was made by stirring 2 mg of Navane in 4 ounces of water then administered orally. The patients were usually afterwards placed on vasodilators such as ace inhibitors and calcium channel blockers.

Problems

The approach used in Applicant's clinical practice of over 2,000 patients, is the approach of using vasodilators to treat migraine headache, to cause improvement in closed head injury symptoms, and to treat vasospasm from any cause. This has also been effective in Attention Deficit Disorder (ADD) and multiple other disorders with cerebral ischemia or vasospasm as a component. A partial list of these disorders include Vascular Seizures, Vertigo, Tinnitis, Post Subarachnoid Hemmorhage Vasospasm secondary to both aneurysm rupture or trauma, Stroke, reversal of a chronic stroke penumbra, autism, depression, Post-Traumatic Stress Syndrome, autism, dyslexia, visual disturbances and blindness, Autism, Tourette's Syndrome, Tics, Tremors. Ataxia and multiple other neurocognitive, neuropsychiatric, and neurological disorders that have vasospasm and ischemia as a common aetiology, systemic disorders with diffuse vascular involvement. i.e. some types of Fibromyalgia and Prinz Metal Angina may also be treated with this approach. The approach to treatment and results are essentially identical in these cases, with minor variations.

However, 10% of patients placed on antihypertensives will develop peripheral hypotension before the vasospasm is successfully treated. In those patients, Navane (Thiothixene) and other antipsychotics of that group, have been found to be an extremely effective central vasodilator without causing peripheral blood pressure changes. These patients may do well on low dose Angiotensin Converting Enzyme Inhibitors. Calcium Channel Blockers. Alpha blockers and/or Nitrates with the use of Navane (Thiothixene) and the other anti=A9psychotics of that group and have excellent resolution of vasospasm.
02747E14E5C

EXAMPLE

Whip-Lash/Breast Implants/Migraine

Applicant has a baseline practice consisting of mainly post-traumatic, closed-head injuries and post-traumatic migraine disorders of which many have attention deficit disorders, (ADD). However, several years ago Applicant had a large number of patients who presented with ADD of which the origin of their problems was associated with silicon breast implants (silicon toxicity). What became evident in evaluating of these patients was that the neuropsychological tests, computerized EEG and Transcranial Artery Doppler results were essentially identical. Another common characteristic in these patients was the waxing and waning nature of at least some of their complaints. Those patients with Attention Deficit Disorder both post-traumatic and in particularly those patients with silicon breast implant disease with MS-like syndrome would have normal neurological examination one day and on another day the exam would be normal. This finding substantiated the patients' complaints of waxing and waning of symptoms and seemed to be related to the degree of physiological or psychological stress the patient experienced when being interviewed or tested.

The degree of abnormality of neurological exams would extend to the point of normal or abnormal Romberg and Tandem Gaits, reflex examinations and Babinski examinations in the same patient. Evoked potential test results varied from normal to abnormal on different days and the testing was performed by the same examiners.

In this same time frame, a series of new medications were developed to treat migraine headaches. As headache was a major complaint of many of these patients, Applicant tried these medications out including Imitrex (Sumatriptan), IM Toradol (Ketoralac) and other medications under direct monitoring. As these patients tend to be intractable, it was not expected that any of these medications would have dramatic results. Rather, it was expected that one or another set of medications might help point the way into using specific classes of medications or approaches. Accordingly, each of these patients, equivalent of a large number of patients, is monitored continuously across the day. The patients are hooked up with EEG's or Brain Stem Auditory Evoked Responses, or VEP's, or Transcranial Dopplers, and across the day would have many of the different short-acting medications tried on them to see which would work and which monitoring tool would be most effective in identifying the improvement.

With respect to the different monitoring tools, some were more helpful than others. It was found that the EEG was not very sensitive. The Brain Stem Auditory Evoked Response and other evoked potential tests were very insensitive tools for monitoring, because of the length of time required to perform the test after short-acting medications were given in IM or sublingual or nasal spray administration route. The Transcranial Doppler consistently appeared to give the best indication as to which medications would work. If an ultrasound showed improvement, the patient invariably also reported improvement in their clinical symptoms. These symptoms included not only headache, but also sensations of confusion, balance disorder, abnormal Romberg or Tandem Gait or other neurological abnormalities. If the medications showed evidence of increasing vasoconstriction on the doppler, the patients who had a headache, frequently reported improvement in the headache, but a worsening of their confusional state or a worsening of other neurological symptoms. Those patients were identified as having improvement on ultrasound with doppler also showed resolution of their headache, but did not show the deterioration in other neurological effects.

This was completely unexpected. The general approach towards migraine and headache has always been that the headache represents a vasodilation and frequently a hyperperfusion state. The aura, of course, represents a vasoconstrictive phase. What our results seemed to suggest was that the doppler, which looks at essentially the area of blood vessels around the base of the brain, was showing vasoconstriction. Vasoconstrictive medicines would relieve the headache presumably through a similar mechanism, as a vasoconstrictive medication probably relieved coronary artery disease. It would relieve it by decreasing the vasodilation that occurs downstream from the area we are able to directly insonate. Unfortunately, if cerebral artery disease is anything like coronary artery disease, that downstream dilation represents an attempt by the body to compensate and maintain perfusion to thus becoming ischemic.

In Applicant's patient population, all medications which resulted in vasoconstriction, relieved the headache, but caused neurological deterioration. As the medication wore off, as documented by the patient's clinical symptoms, sonography data, the patient's neurological abnormalities improved. Similarly, those medicines which resulted in direct vasodilation such as Hydralazine (Apresoline), Nitroglycerin and other medications all resulted in improvement in the patient's headache, but also resulted in improvement of any other neurological abnormalities including balance disorders, gait disorders, hemiparesis, abnormal Babinski's and abnormal reflexes.

Observations Noted Concerning Transcranial Dopplers

A special word about Transcranial Doppler needs to be made. We found that morphology of a Transcranial Doppler Artery Ultrasound is as important as mean flow velocities. In our patients, as they became more normal, and as their fixed deficits and neuropsychological abnormalities resolved etc., the morphology of the wave form would be similar to that of an internal carotid artery tracing. We did not find that there would be elevation of flow readings throughout diastole, as is more commonly published. It is important to identify that the original normative data obtained in 1979, used for "Normals" patients with post-traumatic migraine disorders, "psychogenic seizures", and the interictal migraine phase may not be appropriate. It is important to note that other labs which have done less extensive studies of normal versus non-normal, may have unknowingly used many patients with a history of migraines or whiplash headaches.

Some have not identified the close relationship between degree of vasospasm and clinical abnormalities. This may be due to less lengthy monitoring or evaluations being carried out by those labs in comparison to our own. Equally, the trend clinical correlation is a general one. Remembering hemodynamics, it is important to note that if the blood vessel is constricted, patients do have a limited ability to compensate for the effects of that vasoconstriction by dilating distally to the constricted area. Patients will not be abnormal clinically during the early stages of constriction of an artery. It is only once the downstream area is no longer able to dilate to a degree enough to maintain a significant pressure gradient across the vasoconstricted area that the patient will develop symptoms. It is important to continue to monitor and treat these patients until the sonographic studies return to normal and beyond. Realizing that blood vessels constrict across the day in response to sympathetic nervous system variability, internal steroid release, physiological and psychological stress, including the physiological stress of photic stimulation, driving etc. and thus to obtain an ultrasound at one moment, must be correlated with the patient's clinical symptoms and any complaints of variability across the day.

We also found that over time, chronic, untreated patient studies frequently falsely appear to normalize with a dropping of mean flow velocities. This occurs as the body develops compensating mechanisms to relieve the ischemia. Thus morphology becomes extremely important in identifying those who have ongoing vasoconstrictive disorder intracranially. The development of a pattern as time goes on is to have a blunted upstroke in the systolic portion of the ultrasound, but with an overall mean flow velocity of less than 0.6 meters per second. That blunting, which is also seen in disseminated vascular disease from any cause, is highly suspicious for severe vasospastic disorder. A computerized EEG or standard EEG consistent with brain dysfunction or ischemia, and/or neuropsych testing consistent with variability of cognitive injury (especially with fluctuating cognitive deficits across several hours or days of testing) with ischemia is often helpful as a corroborating study. These are patients who should not be treated initially with Nitroglycerin or other potent medications, but should first have other medications which are direct vasodilators instituted at low doses and slowly advanced as the patient is able to tolerate it. This institution with alternative vasodilators, tends to decrease the incidence of a potentially dangerous nitric oxide sensitivity reaction.

With respect to Nitroglycerin, what we have seen is several time courses of the effect of Nitroglycerin. The first is an acute effect which lasts between 15 and 45 minutes. The method of administration being a patch, pill or sublingual spray determines the rapidity of absorption and distribution. It seems to have a lingering effect for approximately 2 to 3 hours. Nitroglycerin then gets converted into a variety of subsidiary byproducts, all with some vasodilating properties. Each of these medications themselves can accumulate in patients to toxic doses, and can cause a reactive cerebral vasoconstriction. Thus, it is easier to maintain patients on intermittent low dose Nitroglycerin applications, then chronic applications of medication, as the clinical data and clinical response to the vasodilator challenge becomes confused. With respect to Nitric Oxide sensitivity, those patients in Applicant's clinical practice who have not been premedicated with a beta blocker, an alpha blocker or a direct vasodilator such as a calcium channel blocker or an ACE inhibitor, who are given their first dose of Nitric Oxide and developed acute erythema of the nose or face, are having a reactive vasoconstriction and distal vasodilation occurring at the same time. Those patients on Transcranial Doppler Artery Ultrasound will have acute spasm of the arteries and active constrictions and dilations may frequently be seen. Those patients may have a seizure or a stroke or a blackout spell. This problem can be immediately reversed with IM Toradol(ketoralac). Toradol in 90 to 120 mg IM doses causes acute vasodilation on ultrasound in most patients. In lower doses, the Transcranial Doppler Artery Ultrasounds generally do not show significant changes, but the patient reports a symptomatic improvement.

IV Toradol in 30 to 60 mg doses does not cause any improvement on Transcranial Doppler Artery Ultrasound, and patients generally report a sensation of vertebrogenic syndrome with increase in spaciness, confusion, worsening headache and worsening spasm. Although I have not identified this directly, their clinical course is that of a development of a vasoconstricted vertebral or basilar artery syndrome. This probably relates to a carrier drug in the I.V. Toradol solution. Without a change in formulation, Applicant would not recommend the I.V. use of Toradol to reverse acute and life threatening vasospasm or stroke.

Multiple medications over the last several years have now been tried for the vasodilators. A discussion of these will follow. It should be recognized, that Applicant's patients tend to be the most severe cases in our area. Accordingly, for me, the medications that have been most effective have also been among the strongest. The less strong medication will undoubtedly be very helpful in less severe cases. In all cases, as the vasospasm may be subclinical or affecting portions of their cognitive abilities that they do not routinely use. patients can not be considered as reliable in identifying when the vasospasm is resolved. Accordingly, ongoing monitoring of therapy with functional tests such as EEG or Neuropsych testing and imaging tests like ultrasound are vital for evaluation of response to therapy.

With respect to Beta Blockers, Inderal (Propranolol), Tenormin (Atenolol), Lopressor (Metoprolol Tartrate) and Normodyne (Labetolol) have all been tried. None of these have been significantly effective at vasodilation. However, when using vasodilators, patients will frequently notice waxing and waning of their effectiveness. This is especially noticeable in patients who are beginning to be tapered off their medications due to good responses, and thus cannot tolerate higher doses of medications of vasodilators, but still have residual vasospasm. In these patients, Inderal has been extremely effective in smoothing out the sympathetic nervous system excitability that may be seen. The other medications have not been as effective, although probably are useful in blunting any acute response to Nitroglycerin administration from a hypersensitive Nitric Oxide response, if the patient is prone to such a response.

Alpha blockers have been tried. Hytrin (Terazosin) has not been found to be effective. Catapress (Clonidine) has been extremely effective. Minipress (Prazosin) has been significantly effective and frequently better tolerated in the long run than Clonidine, although in Applicant's patients, it seems to treat the problem successfully enough to prevent the symptoms, but not enough to allow complete resolution of the vasospasm. Cardura (Doxazosin) has been a relatively mild medication. Aldomet (Methyldopa) has been useful in some patients. Reserpine has been an extremely effective medication. In the short term, it is helpful due to the parasympathomimetic effect, which tends to decrease the activity of the Sumpathetic nervous system. Later, its direct sympatholytic action is very effective. Frequently, a dose needs to be adjusted downward approximately 6–10 weeks after institution of therapy. It has even been useful in treating migraine induced depression due to chronic vasospasm with or without headache in those patients who could not tolerate other vasodilators. Clonidine has also been useful in these depressed patients who could not respond to other vasodilating medications.

ACE inhibitors have been tried. With use of ACE inhibitors and concomitant administration of low dose Nitroglycerin, $\frac{1}{10}$th inch once a day to several times a day, most patients may be eventually weaned from the use of oral medications, although Applicant do tend to maintain them on low dose Nitroglycerin in perpetuity. Other Angiotensin Converting Enzyme Inhibitors, including Capoten (Captopril), Altace (Ramipril), Lotensin (Benazepril), Monopril (Fosinopril), Prinivil (Lisinopril), Vasotech (Enalapril), and an ACE inhibitor have also been tried. I suspect that ACE inhibitors work the best due to its activity on the Nitric Oxide pathway. It is most effective at reversing the vasospasm when used in conjunction with low dose nitrates.

Calcium channel blockers have been tried. The most effective has been Dynacirc (Isradapine). Much less effective have been, in descending order of effectiveness, Nifedipine. Nimodopine, Plendil (Felodipine), Dilacor (Diltiazem), Cardene (Nicardipine) and. Norvasc (Amlodopine) and finally, Verapamil.

Other agents that deserve special mention include Toradol IM in doses of 90–120mg. In lower doses., this is not so effective. Unfortunately, due to the new FDA guidelines. Applicant no longer use this medication in these doses. Hydralazine is effective, but tends to cause significant blood pressure changes in these patients. Interestingly though, Hydralazine tends to improve the morphology of the diastolic flow component dramatically which in view of Hydralazine's effect on arterioles, bolsters the perspective that the diastolic phase of the Transcranial Doppler is a good indicator of downstream runoff.

Psychiatric agents frequently have vasoactive effects. Prozac and other non-vasoconstricting medications are helpful. Those known to cause vasoconstriction tend to aggravate the spasm and neurological abnormalities. Antipsychotic agents have also been used. Several of Applicant's patients who ApplicanT will be reporting on later, were psychotic, and responded well to these medication s and had significant vasospasm identified on ultrasound which improved after the administration of medication. Of the antipsychotics, Navanne (Thiothixene) has been the most effective. Thorazine (Chlormromazine) has been moderately effective. Respiradol has generally improved the patient's symptoms, but had no significant improvement on ultrasound. It has been less well-tolerated in comparison with Thorazine and Navane. Interestingly enough, most of the patients who were placed on Navane, did not continue to require Navane two to three months after starting the medication, and were able to be weaned from that and had better response to their other vasodilators. In general, Navane was used as a first line drug in patients who had severe elevations of Transcranial Doppler Artery mean flow velocities greater than 1.3, and we would generally expect 50% improvement in the Transcranial Doppler Artery Ultrasound within a half hour of administering Navane by liquid solution. The solution was made by stirring 2 mg of Navane in 4 ounces of water then administered orally. The patients were usually afterwards placed on vasodilators such as ACE inhibitors and Calcium channel blockers. Mellaril (Thioridazine) has had no significant effects.

Of the Anti-epileptic drugs, including Dilantin (Phenytoin), Tegretol (Carbamazepine) and Depakote (Valproate), none of the medications in therapeutic doses have changed the vasospasm, but all have improved in some patients the EEG abnormalities and their neurocognitive or neurological complaints.

Problems

The approach used in Applicant's clinical practice of over 2,000 patients, is the approach of using vasodilators to treat migraine headache, to cause improvement in closed head injury symptoms, and to treat disorders diverse and including seizures, stroke, syncope, attention deficit disorder, vertigo, autism, depression, psychosis, transient global amnesia. Multiple Sclerosis and Multiple Sclerosis like syndrome, but not limited to these disorders.

However, approximately 10% of patients placed on antihypertensives will develop peripheral hypotension before the vasospasm is successfully treated. These patients appear to have an increased peripheral vasodilation to central vasodilation in response to the medication.

In these patients, several approaches may be used. The pharmacological approach is to mix several medications of different classes at submaximal doses to achieve a synergistic response. An alternative approach is to use medications such a Toradol or antipsychotic medications that also dilate primarily the vascular bed of the Central Nervous System and not that of the peripheral. In those patients, Navane and the antipsychotic of that group, have been found to be an extremely effective central vasodilator without causing peripheral blood pressure changes. Patients placed on these agents are frequently able to tolerate low dose ACE inhibitors. Calcium Channel agents, or other peripheral vasodilators without developing hypotension and still have excellent resolution of vasospasm. The structural approach is to search for an underlying aggravating problem affecting the sympathetic nervous system. This is usually caused by an injured area of the body which may include joint injuries, disk injuries, nerve injuries, etc. One of Applicant's patients developed severe neurocognitive problems and neuropsych abnormalities, EEG problems, and vasospasm, from a Carpal Tunnel Syndrome. The correction of that problem, or any other irritant to the Sympathetic Nervous system by blocking the irritant or removing it, may result in a decrease in the autonomic hyperactivity, and an improved response to medication. A third approach is to sympathetically denervate the vasculature. This may be partially performed with Epidural Steroid Injections with or without anaesthetic, Facet or Perifacet blocks, Rhyzolysis, Stellate Ganglion Blocks and Neurolyses and similar procedures. In Applicant's practice, procedures oriented towards the innervation of the Carotid arteries tend to cause Anterior and Middle Cerebral artery relaxation. This clinically results in increase concentration/memory and decreased mood/personality problems and language problems and other frontal and temporal lobe disorders. Posterior circulation denervation tends to decrease occipital headaches, and improve balance, vertigo, and visual complaints and have secondary cognitive effects (probably through perforating vessel contributions). Blocks tend to work for a dramatically shorter period of time than do neurolysis procedures.

Chiropractic procedures may be very helpful as may Biofeedback and counselling procedures to decrease the Autonomic hyperactivity. These techniques may also be useful adjuncts to treatment in the chronic patient. Stroke.V11

What is claimed is:

1. A method of operating a titration system for the treatment of chronic noncardiac diseases comprising vasospasm or other symptom alleviatable by smooth muscle relaxation, said system comprising a flow device and a dosage device and said method comprising in combination:
    a) operating the flow device to measure blood flow in at least one area,
    b) applying the dosage device for administering a first dosage of a vasodilator,
    c) operating the flow device for remeasuring blood flow, and; d) reapplying the dosage device to administer an adjusted further dosage of a vasodilator, the further dosage being adjusted in response to said remeasured blood flow,
    e) repeating the operation of said system over a period of days while titrating said dosage according to still further measurements of blood flow to maintain optimal blood flow velocity.

2. A method according to claim 1 wherein the symptoms comprise cerebral vasospasm.

3. A method according to claim 1 wherein the measuring device utilizes a technique selected from the group consisting of Transcranial Doppler (TCD), quantitative electroencephalogram and determining relative vessel diameter.

4. A method according to claim 1 wherein the flow device measures blood flow as Mean Fluid Velocity (MFV) in at least one intracranial vessel.

5. A method according to claim 4 wherein the MFV rises above about 0.4 meters/minute during vasospasms.

6. A method according to claim 1 wherein the treatment is continued for from about 5 to 250 weeks.

7. A method according to claim 1 wherein the vasodilator is selected from the group consisting of Nitroglycerin in pill, patch, ointment, cream, inhaler, spray and other forms, Nitroglycerin equivalents and substitutes, such as p.o. clonidine, Dynacirc (istadipine), hydrazine, nifedipine, and medicines from the empirical group combinations of the foregoing.

8. A method according to claim 1 wherein the disease is selected from the group consisting of whiplash, closed head injury with vasospasm, attention deficit disorder with vasospasm, migraine with inter-octal evidence of vasospasm, syncope or blackout spells of unknown actiology with evidence of vasospasm, seizure with evidence of vasospasm, and dementia with evidence of vasospasm, concussion and post-concussion syndrome with evidence of vasospasm, migraine, sympathetic vasospasm associated with breast implants, and cerebral vasospasm. fibromyalgia, gastric disorders and other systemic disorders, psychosis, other psychiatric disease, attention deficit disorder and systemic disorders dyslexia, memory disturbances, depression, psychosis, reflex sympathetic dystrophy, mood disorders and sensory motor disorders; transient ischemic attack (TIA), pseudoseizure, hemibalism, and stroke; tremor, Parkinson's disease, torticollis, electrical shock trauma, attention deficit disorder, concussion and post concussion syndrome, comprising vasospasm as a component.

9. A method of claim 1 wherein the patient treated presents with transient or continuous TCD Mean Flow Velocities (MFV) of greater than 0.1 meter per second.

10. A method of treatment of intracranial vasospasms comprising intermittently applying a vasodilator and measuring transcranial doppler mean flow velocity, and titrating dosage as the vasospasms reduce in frequency and/or severity.

11. A method of claim 1 wherein the treatment is applied to a patient who presents with transient or continuous TCD Mean Flow Velocities (MFV) of greater than 0.3 meters per second.

12. A method according to claim 1 wherein the disease is selected from the group consisting of fibromyalgia, gastric disorders and other systemic disorders, psychosis, other psychiatric disease, attention deficit disorder and systemic disorders, comprising vasospasm as a component.

13. A method according to claim 1 wherein the disease is selected from the group consisting of systemic disorders comprising vasospasm as a component.

14. A method for operating a titration system for diagnosing and treating a disease caused at least partially by insufficient cerebral perfusion, comprising in combination: operating a flow device to test for the presence of a continued diastolic flow beyond end diastolic velocity as an indication of vasospasm, applying a dosage device which administers a vasospasm-reducing dosage of a medicine selected from the empirical group of medications which have the common characteristic of causing smooth muscle relaxation and/or which reduce pulmonary capillary wedge pressure, smooth muscle relaxation and/or which reduce pulmonary capillary wedge pressure, reoperating said flow device for testing over time and adjusting said dosage device to titrate said dosage to minimize occurrence and severity of said indications of vasospasm.

* * * * *